(12) United States Patent
Nakayama et al.

(10) Patent No.: US 10,100,107 B2
(45) Date of Patent: Oct. 16, 2018

(54) METHOD FOR IDENTIFYING A COMPOUND USEFUL WITH MYOSIN REGULATORY LIGHT CHAIN POLYPEPTIDE ANTIBODY FOR TREATMENT OF AN INFLAMMATORY DISEASE

(71) Applicant: National University Corporation Chiba University, Chiba (JP)

(72) Inventors: Toshinori Nakayama, Chiba (JP); Hiroyuki Hosokawa, Chiba (JP); Koji Tokoyoda, Chiba (JP); Koji Hayashizaki, Chiba (JP); Akane Suzuki, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 15/667,644

(22) Filed: Aug. 3, 2017

(65) Prior Publication Data

US 2017/0334982 A1  Nov. 23, 2017

Related U.S. Application Data

(62) Division of application No. 14/893,122, filed as application No. PCT/JP2014/064399 on May 30, 2014, now Pat. No. 9,758,574.

(30) Foreign Application Priority Data

May 30, 2013 (JP) .................................. 2013-114388

(51) Int. Cl.
| | | |
|---|---|---|
| *G01N 33/53* | (2006.01) | |
| *A61P 11/00* | (2006.01) | |
| *A61P 37/08* | (2006.01) | |
| *A61P 37/02* | (2006.01) | |
| *C07K 16/18* | (2006.01) | |
| *G01N 33/566* | (2006.01) | |
| *G01N 33/68* | (2006.01) | |
| *C07K 14/47* | (2006.01) | |
| *A61K 39/395* | (2006.01) | |
| *A61K 39/00* | (2006.01) | |

(52) U.S. Cl.
CPC .......... *C07K 16/18* (2013.01); *G01N 33/566* (2013.01); *G01N 33/6887* (2013.01); *A61K 39/395* (2013.01); *A61K 2039/505* (2013.01); *C07K 14/4716* (2013.01); *C07K 2317/34* (2013.01); *G01N 2333/4712* (2013.01); *G01N 2333/70596* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 2009/0220487 A1 | 9/2009 | Schwartz et al. | |
| 2010/0093789 A1 | 4/2010 | Yamada et al. | |
| 2016/0102139 A1 | 4/2016 | Nakayama et al. | |

OTHER PUBLICATIONS

Hayashizaki et al (2016. Sci Immunol. 1: 1-10).*
International Search Report issued in corresponding International Patent Application No. PCT/JP2014/064399 dated Aug. 5, 2014 (6 pages).
Ikegaki, I., "Novel Protein Kinase Inhibitor: Fasudil Pharmacological Effects on Cerebral Vasospasm following Subarachnoid Hemorrhage," Brain 21, vol. 3, No. 4, 2000, pp. 453-456 (19 pages) (English translation included).
Xu et al., "Nonmuscle myosin light-chain kinase mediates neutrophil transmigration in sepsis-induced lung inflammation by activating beta2 integrins," Nature Immunology, vol. 9, No. 8, 2008, pp. 880-886 (16 pages).
Benjamini et al., Immunology: A Short Course, Second Edition, Wiley-Liss, 1991, p. 40 only (3 pages).
Datasheet for sc-19849-R, Santa Cruz Biotechnology, Inc., http://datasheets.scbt.com/sc-19849.pdf, (1 page).
O'Hara et al., "Cholangiocyte Myosin IIB Is Required for Localized Aggregation of Sodium Glucose Cotransporter 1 to Sites of Cryptosporidium parvum Cellular Invasion and Facilitates Parasite Internalization," Infection and Immunity, vol. 78, No. 7, 2010, pp. 2927-2936.
Park et al., "Myosin regulatory light chains are required to maintain the stability of myosin II and cellular integrity," Biochem. J., (2011) 434, pp. 171-180.

* cited by examiner

*Primary Examiner* — Zachary C Howard
(74) *Attorney, Agent, or Firm* — Kilyk & Bowersox, P.L.L.C.

(57) ABSTRACT

Provided is a means for inhibiting a function of CD69, whereby allowing suppression of an inflammatory response. That is, provided are: a composition for treating an inflammatory disease which includes an antibody that specifically recognizes a myosin regulatory light chain polypeptide (hereinafter abbreviated as Myl), preferably Myl9, Myl12a, and Myl12b, and inhibits a result of an effect of coexistence of Myl with CD69; a method of treating an inflammatory disease, including administering, to a subject diagnosed as having an inflammatory disease, a therapeutically effective amount of the antibody; and a method of identifying a compound that inhibits a result of an effect of coexistence of Myl with CD69, and a method of identifying a candidate compound for treating an inflammatory disease, including selecting a compound that inhibits the result.

7 Claims, 8 Drawing Sheets

Specification includes a Sequence Listing.

METHOD FOR IDENTIFYING A COMPOUND USEFUL WITH MYOSIN REGULATORY LIGHT CHAIN POLYPEPTIDE ANTIBODY FOR TREATMENT OF AN INFLAMMATORY DISEASE

This application is a divisional application of U.S. patent application Ser. No. 14/893,122, filed Nov. 23, 2015, which is a National Stage Application of PCT/JP2014/064399, filed May 30, 2014, which claims priority from Japanese Patent Application No. 2013-114388, filed May 30, 2013.

TECHNICAL FIELD

The present invention relates to a composition for treating an inflammatory disease, which comprises an anti-myosin regulatory light chain polypeptide antibody. Hereinafter, myosin regulatory light chain polypeptide is abbreviated as Myl. The antibody inhibits a result of an effect of coexistence of Myl with CD69. Specifically, the present invention relates to a composition for treating an inflammatory disease, such as airway inflammatory disease, which comprises anti-Myl9 antibody that inhibits a result of an effect of coexistence of Myl9 with CD69, or anti-Myl12 antibody that inhibits a result of an effect of coexistence of Myl12 with CD69. The present invention also relates to a method of treating an inflammatory disease, comprising administrating, to a subject diagnosed as having an inflammatory disease, the antibody in an amount effective in treating the inflammatory disease. The present invention also relates to a method of identifying a candidate compound for treating an inflammatory disease, which inhibits a result of an effect of coexistence of Myl with CD69.

BACKGROUND ART

A myosin regulatory light chain is one of the subunits constituting a multi-subunit protein product, myosin. It is known that myosin is a hexamer formed by two heavy chains, two regulatory light chains, and two essential light chains, and is a motor protein that causes actin filament contraction, by using energy generated by hydrolyzing adenosine triphosphate (hereinafter abbreviated as ATP). All myosin light chains are members of calmodulin superfamily. Myl9, Myl12a, and Myl12b are known as the myosin regulatory light chain and Myl6 is known as the myosin essential light chain.

CD69 is a type II transmembrane protein belonging to C-type lectin family. CD69 is widely used as an indicator of lymphocyte activation as an early activation marker molecule because the expression level is increased within a few hours after stimulating T cells or B cells (Non Patent Literature 1). In addition, CD69 is found to be expressed also in T cells at a selection stage during differentiation in thymus gland (Non Patent Literatures 2 and 3). Further, it has been reported that CD69 is also expressed in memory CD4 T cells being maintained in bone marrow and CD69 is important for migration of activated CD4 T cells to bone marrow and subsequent maintenance of memory CD4 T cells (Non Patent Literature 4). It is supposed that CD69 has a function to enhance signaling from an antigen receptor as a coreceptor, but details thereof are unclear. The ligand of CD69 has not been identified yet. CD69 is constitutively expressed in platelets and is also expressed in activated neutrophils, eosinophils, and the like, and therefore it is supposed that CD69 has a role in functional expression of platelets and local inflammatory responses. In addition, it is revealed that CD69 on neutrophils plays a key role in development of arthritis (Non Patent Literature 5). It has also been reported that CD69 on CD4 T cells controls allergic airway inflammation and the antibody to CD69 suppresses allergic airway inflammation (Non Patent Literature 6). In addition, it has been reported that in CD69-deficient mice, COPD induced by cigarette smoke and lung fibrosis induced by bleomycin are attenuated (Non Patent Literatures 7 and 8).

CITATION LIST

Non Patent Literature

[NPL 1] Testi, R. et al. The CD69 receptor: a multipurpose cell-surface trigger for hematopoietic cells. Immunol. Today 15: 479-483, 1994

[NPL 2] Yamashita, I. et al. CD69 cell surface expression identifies developing thymocytes which audition for T cell antigen receptor-mediated positive selection. Int. Immunol. 5:1139-1150, 1993

[NPL 3] Nakayama, T et al. The generation of mature, single-positive thymocytes in vivo is dysregulated by CD69 blockade or overexpression. J. Immunol. 168: 87-94, 2002

[NPL 4] Shinoda, K. et al.: Type II membrane protein CD69 regulates the formation of resting T-helper memory. Proc. Natl. Acad. Sci. 109; 7409-7414, 2012

[NPL 5] Murata, K. et al.: CD69-null mice protected from arthritis induced with anti-type II collagen antibodies. Int. Immunol. 15: 987-992, 2003

[NPL 6] Miki-Hosokawa, T. et al.: CD69 controls the pathogenesis of allergic airway inflammation. J. Immunol. 183; 8203-8215, 2009

[NPL 7] Yamauchi, K. et al. Attenuation of lung inflammation and fibrosis in CD69-deficient mice after intratracheal bleomycin. Respir Res. 12; 131, 2011

[NPL 8] Tsuyusaki, J. et al. Cigarette smoke-induced pulmonary inflammation is attenuated in CD69-deficient mice. J. Recept Signal Transduct Res. 31; 434-439, 2011

SUMMARY OF INVENTION

Problem to be Solved by the Invention

There are many reports indicating the involvement of CD69 in inflammatory responses. Therefore, it is considered that when the function of CD69 is inhibited, the inflammatory responses can be suppressed, and eventually, inflammatory diseases can be prevented and treated. Meanwhile, a method of treating allergic inflammation in which CD69 is targeted may affect various cells expressing CD69, and hence side effects need to be taken into account.

An object of the present invention is to provide means for inhibiting the function of CD69, and further to suppress an inflammatory response by the means.

Means for Solving Problem

The inventors of the present invention have made extensive investigations to achieve the object and have found Myl9, Myl12a, and Myl12b as proteins acting on CD69. In addition, it has been revealed that when CD4 T cells activated by stimulation using anti-T cell receptor antibody to express CD69 were transferred into a mouse via tail vein, the activated CD4 T cells migrated to bone marrow and the migration of the activated CD4 T cells to bone marrow was inhibited by preliminary administration of the antibody which recognized all of Myl9, Myl12a, and Myl12b (hereinafter sometimes referred to as anti-Myl9/12 antibody). Further, it was revealed that when the anti-Myl9/12 antibody was administered to a mouse in which airway inflammation was induced, the number of eosinophils in bronchoalveolar lavage was decreased and an increase in methacholine-induced airway resistance was suppressed compared to a mouse to which a control antibody was administered. The present invention has been achieved based on those findings.

That is, the present invention relates to a composition for treating an inflammatory disease, the composition comprising an antibody that specifically recognizes a myosin regulatory light chain polypeptide, which is hereinafter abbreviated as Myl, and inhibits a result of an effect of coexistence of Myl with CD69.

The present invention also relates to the treatment composition, in which the effect of coexistence of Myl with CD69 is a binding of Myl with CD69.

The present invention also relates to any one of the treatment compositions, in which the Myl is any one or more selected from the group consisting of Myl9, Myl12a, and Myl12b.

The present invention also relates to any one of the treatment compositions, in which the antibody is an antibody that specifically recognizes a partial amino acid sequence of Myl9, Myl12a, or Myl12b, wherein the partial amino acid sequence is an amino acid sequence of SEQ ID NO: 24 in a sequence listing.

The present invention also relates to any one of the treatment compositions, in which the inflammatory disease is an airway inflammatory disease.

The present invention also relates to any one of the treatment compositions, in which the inflammatory disease is an allergic airway inflammatory disease.

The present invention also relates to a method of identifying a compound that inhibits a result of an effect of coexistence of Myl with CD69, the method comprising: allowing Myl to coexist with CD69 in the presence of a test compound; subsequently measuring an effect of coexistence of Myl with CD69; and determining that the test compound inhibits a result of an effect of coexistence of Myl with CD69 when reduction or disappearance of the effect is detected.

The present invention also relates to the method of identifying a compound, in which the effect of coexistence of Myl with CD69 is a binding of Myl with CD69.

The present invention also relates to any one of the methods of identifying a compound, in which the Myl is any one selected from the group consisting of Myl9, Myl12a, and Myl12b.

The present invention also relates to a method of identifying a candidate compound that serves as an active ingredient of a composition for treating an inflammatory disease, the method comprising selecting a compound that inhibits a result of an effect of coexistence of Myl with CD69.

The present invention also relates to the method of identifying a candidate compound, in which the effect of coexistence of Myl with CD69 is a binding of Myl with CD69.

The present invention also relates to any one of the methods of identifying a candidate compound, in which the Myl is any one selected from the group consisting of Myl9, Myl12a, and Myl12b.

The present invention also relates to a method of treating an inflammatory disease, comprising administering, to a subject diagnosed as having an inflammatory disease, an antibody that specifically recognizes Myl and inhibits a result of an effect of coexistence of Myl with CD69, in an amount effective in treating the inflammatory disease.

The present invention also relates to the treatment method, in which the effect of coexistence of Myl with CD69 is a binding of Myl with CD69.

The present invention also relates to any one of the treatment methods, in which the Myl is any one or more selected from the group consisting of Myl9, Myl12a, and Myl12b.

The present invention also relates to any one of the treatment methods, in which the antibody is an antibody that specifically recognizes a partial amino acid sequence of Myl9, Myl12a, or Myl12b, wherein the partial amino acid sequence is an amino acid sequence of SEQ ID NO: 24 in a sequence listing.

The present invention also relates to any one of the treatment methods, in which the inflammatory disease is an airway inflammatory disease.

The present invention also relates to any one of the treatment methods, in which the inflammatory disease is an allergic airway inflammatory disease.

Advantageous Effects of Invention

According to one embodiment of the present invention, the composition for treating an inflammatory disease, such as an allergic airway inflammatory disease, which includes an anti-myosin regulatory light chain polypeptide antibody, can be provided. According to another embodiment of the present invention, the method of treating an inflammatory disease, such as an allergic airway inflammatory disease, which includes administrating an anti-myosin regulatory light chain polypeptide antibody to a subject, can be provided.

According to other embodiments of the present invention, the method of identifying a compound that inhibits a result of an effect of coexistence of a myosin regulatory light chain polypeptide with CD69, and the method of identifying a candidate compound that serves as an active ingredient of a composition for treating an inflammatory disease, which includes selecting a compound that inhibits a result of an effect of coexistence of a myosin regulatory light chain polypeptide with CD69, can be provided.

It can be considered that the anti-myosin regulatory light chain polypeptide antibody inhibits the effect of the myosin regulatory light chain polypeptide that modulates the function of CD69 in coexistence of the myosin regulatory light chain polypeptide with CD69, and therefore the antibody inhibits the function of CD69. The composition including the anti-myosin regulatory light chain polypeptide antibody according to the embodiment of the present invention has less side effects because the target of the composition is the myosin regulatory light chain polypeptide that is specifically expressed when inflammation is induced. In addition, the composition has a high possibility of controlling also memory CD4 T cells expressing CD69, which migrate to and are maintained in bone marrow. Therefore, the composition can be expected to exhibit inhibitory effects on a wide variety of inflammations, such as a chronic inflammation in which the above-mentioned targets are involved.

BRIEF DESCRIPTION OF DRAWINGS

In FIG. 1A, IP represents immunoprecipitation, Anti-GST represents anti-GST antibody, GST-mock represents GST protein alone, and BM total lysate represents a bone marrow extract (Example 1).

In FIG. 1B, the bold line represents an amino acid sequence obtained by LC-MS/MS analysis (Example 1).

In FIG. 1C, BM lysate represents a bone marrow extract, IP:Anti-Flag represents immunoprecipitation using anti-Flag peptide antibody, and IB:Myl9/12 represents immunoblotting using anti-Myl9/12 antibody. Whole indicates immunoblotting of a bone marrow extract using anti Myl9/12 antibody (Example 1).

In FIG. 2A, IB:Anti-Flag represents immunoblotting using anti-Flag peptide antibody (Example 2).

In FIG. 2B, IP:Anti-Flag represents immunoprecipitation using anti-Flag peptide antibody, and IB:Anti-Flag represents immunoblotting using anti-Flag peptide antibody. In addition, Resting represents non-stimulated cells, M represents cells to which Flag peptide was introduced, and 69 represents cells to which Flag-mCD69FL was introduced (Example 2).

In FIG. 2D, BM represents a bone marrow extract, blood represents peripheral blood, Control represents rabbit IgG antibody, and IB:Anti-Myl9/12 represents immunoblotting using anti-Myl9/12 antibody (Example 2).

In FIG. 3B, IB:Myl9/12 represents immunoblotting using anti-Myl9/12 antibody and IB:α-tubulin represents immunoblotting using anti-α-tubulin antibody (Example 3).

In FIG. 3E, Whole represents the whole cells of bone marrow (Example 3).

In FIG. 4, Human represents the amino acid sequence of human Myl9 isoform a and Mouse represents the amino acid sequence of mouse Myl9. Amino acid sequences in the middle indicate the results of comparisons between the amino acid sequences of human Myl9 isoform a and mouse Myl9 and "+" represents that amino acid residues are different from each other.

In FIG. 5B, Control represents non-inflammation induction and Inhalation represents inflammation induction. In addition, IB:Myl9/12 represents immunoblotting using anti-Myl9/12 antibody, IB:α-tubulin represents immunoblotting using anti-α-tubulin antibody (Example 4).

In FIG. 5C, Total represents the whole cells. In FIG. 5C, No treat represents a non-inflammation induction group (Example 4).

DETAILED DESCRIPTION OF THE INVENTION

Figures 1A, 1B:
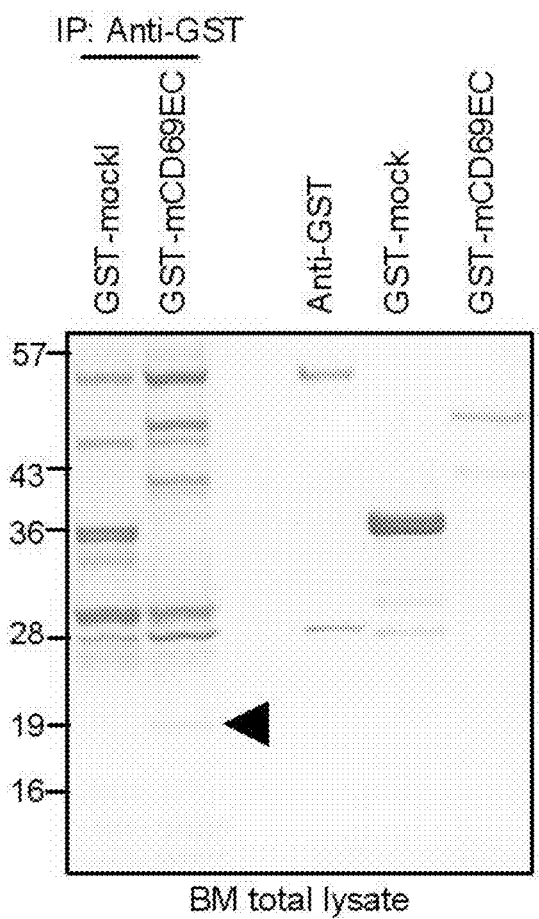
FIG. 1A is an image for showing that a fused protein of mouse CD69 extracellular domain protein and glutathione S-transferase (GST-mCD69EC) was mixed with a bone marrow extract and then the mixture was subjected to pulldown assay using anti-GST antibody, and consequently, a specific band (arrowhead) indicating a protein coprecipitated with GST-mCD69EC was detected.
FIG. 1B is a view for illustrating the protein contained in the band detected in FIG. 1A, that is, the amino acid sequence of mouse Myl9 and the amino acid sequences of mouse Myl12a and Myl12b, which are homologous with Myl9. Identification of the protein was performed by LC-MS/MS analysis.

The present invention relates to use of an antibody that specifically recognizes Myl and inhibits a result of an effect of coexistence of Myl with CD69, in the production of a drug or a pharmaceutical composition for treating an inflammatory disease or in the treatment of an inflammatory disease.

That is, the present invention relates to a drug or a pharmaceutical composition that is used for treating an inflammatory disease. The drug or the pharmaceutical composition for treating an inflammatory disease according to the present invention contains an antibody that specifically recognizes Myl and inhibits a result of an effect of coexistence of Myl with CD69, in an amount effective in treating or alleviating an inflammatory disease.

The present invention also relates to a method of treating an inflammatory disease. The method of treating an inflammatory disease according to the present invention includes administrating, to a subject diagnosed as having an inflammatory disease, an antibody that specifically recognizes Myl and inhibits a result of an effect of coexistence of Myl with CD69, in an amount effective in treating an inflammatory disease.

The present invention also relates to a method of identifying a compound that inhibits a result of an effect of coexistence of Myl with CD69. The method includes: allowing Myl to coexist with CD69 in the presence of a test compound; subsequently measuring an effect in coexistence of Myl with CD69; and determining that the test compound inhibits a result of an effect of coexistence of Myl with CD69 when reduction or disappearance of the effect is detected.

The present invention also relates to a method of identifying a candidate compound that serves as an active ingredient of a composition for treating an inflammatory disease, which includes selecting a compound that inhibits a result of an effect of coexistence of Myl with CD69.

In the present invention, "Myl" is preferably Myl9, Myl12a, or Myl12b, more preferably Myl9. In addition, Myl is preferably a human-derived protein but may be a mammal-derived protein having a function similar to that of the human-derived protein and having structural homology with the human-derived protein, for example, a protein derived from mice, horses, sheep, cattle, dogs, monkeys, cats, bears, rats, or rabbits.

Amino acid sequences of Myl9, Myl12a, and Myl12b and nucleotide sequences of nucleic acids encoding Myl9, Myl12a, and Myl12b are well known to a person skilled in the art. Nucleic acids encoding human-derived Myl9 may be, for example, DNA encoding Myl9 isoform a represented by the nucleotide sequence (NM_006097.4) of SEQ ID NO: 1 and DNA encoding Myl9 isoform b represented by the nucleotide sequence (NM_181526.2) of SEQ ID NO: 3. In addition, human-derived Myl9 isoform a and isoform b may be, for example, polypeptides represented by the amino acid sequences (NP_006088.2 and NP_852667.1) of SEQ ID NOS: 2 and 4, respectively. Myl 9 isoform b lacks amino acid residues at positions 63 to 116 in the amino acid sequence of isoform a and is expressed in smooth muscle cells or some of other cells. A nucleic acid encoding human-derived Myl12a may be, for example, DNA represented by the nucleotide sequence (NM_006471.2) of SEQ ID NO: 5. In addition, human-derived Myl12a may be, for example, a polypeptide represented by the amino acid sequence (NP_006462.1) of SEQ ID NO: 6. Nucleic acids encoding human-derived Myl12b may be, for example, transcript variants 1, 2, and 3 represented by the nucleotide sequences (NM_001144944.1, NM_033546.3, and NM_001144945.1) of SEQ ID NOS: 7, 9, and 11. Amino acid sequences encoded by those transcript variants are set forth in SEQ ID NOS: 8, 10, and 12 (NP_001138416.1, NP_291024.1, and NP_001138417.1). A nucleic acid encoding mouse-derived Myl9 may be, for example, DNA represented by the nucleotide sequence (NM_172118.1) of SEQ ID NO: 13. In addition, mouse-derived Myl9 may be, for example, a polypeptide represented by the amino acid sequence of SEQ ID NO: 14. A nucleic acid encoding mouse-derived Myl12a may be, for example, DNA represented by the nucleotide sequence (NM_026064.2) of SEQ ID NO: 15. In addition, mouse-derived Myl12a may be, for example, polypeptide represented by the amino acid sequence of SEQ ID NO: 16. A nucleic acid encoding mouse-derived Myl12b may be, for example, DNA represented by the nucleotide sequence (NM_023402.2) of SEQ ID NO: 17. In addition, mouse-derived Myl12b maybe, for example, a polypeptide represented by the amino acid sequence of SEQ ID NO: 18. It should be noted that the numbers represented as NM_XXXXXX.X, NM_XXXXXXXXX.X, NP_XXXXXX.X, NP_XXXXXXXXX.X, and the like (in this case, X represents a number) are accession numbers of genes or proteins registered to GenBank of National Center for Biotechnology Information (NCBI) of National Library of Medicine.

The phrase "antibody that specifically recognizes Myl" means an antibody that more selectively recognizes Myl compared with a protein except Myl which has low amino acid sequence homology with Myl. For example, the antibody that specifically recognizes Myl means an antibody that more selectively acts on Myl or more selectively binds with Myl than a protein except Myl, which has low amino acid sequence homology with Myl. The presence or absence of the recognition by the antibody may be determined by a known antigen-antibody reaction. Myl9 and Myl12a, and Myl9 and Myl12b have an amino acid sequence homology of 94.2% and 93.6%, respectively, and Myl12a and Myl12b have an amino acid sequence homology of 97.7%. Thus, the antibody that specifically recognizes Myl9 specifically recognizes Myl12a and Myl12b. Conversely, the antibody that specifically recognizes Myl12a and Myl12b specifically recognizes Myl9.

The antibody according to the present invention may be preferably, for example, an antibody that specifically recognizes Myl9, an antibody that specifically recognizes Myl12a, or an antibody that specifically recognizes Myl12b, more preferably an antibody that recognizes all of Myl9, Myl12a, and Myl12b. For example, the antibody may be an antibody that specifically recognizes a partial amino acid sequence having high homology among amino acid sequences of Myl9, Myl12a, and Myl12b. As such partial amino acid sequence, there may be given an amino acid sequence of SEQ ID NO: 24 in the sequence listing. The amino acid sequence of SEQ ID NO: 24 in the sequence listing is a partial amino acid sequence which is located in the N-terminal region of the amino acid sequence of Myl9 and has extremely high homology with amino acid sequences in the corresponding regions of Myl12a and Myl12b. In addition, the antibody that specifically recognizes a region including the amino acid sequence of SEQ ID NO: 24 inhibits the result of the effect of coexistence of Myl with CD69, and hence it is supposed that this region includes an action site between Myl and CD69.

The phrase "effect of coexistence of Myl with CD69" means an interaction between Myl and CD69 occurring when Myl and CD69 coexist. The term "interaction" means that for example, two proteins of the same or different kinds specifically act on each other, and resulting in change of the function of one or both of the proteins, for example, enhance or decrease. The phrase "specifically act" means acting more selectively on proteins having the action compared to proteins other than the proteins having the action. That is, it can be said that the "effect of coexistence of Myl with CD69" refers to an action of Myl that induces the function of CD69. In addition, as the "effect of coexistence of Myl with CD69", there may be given a binding between Myl and CD69.

The phrase "result of an effect of coexistence of Myl with CD69" means a change in function of CD69 resulting from the effect of coexistence of Myl with CD69, for example, expression or enhancement of the function of CD69 or a change in physiological function caused by a change in function of CD69 by the action of Myl. As the "result of an effect of coexistence of Myl with CD69, there may be given migration of CD4 T cells expressing CD69 to bone marrow.

The phrase "inhibit an result of an effect of coexistence of Myl with CD69" means that the result of the effect of coexistence of Myl with CD69 is reduced.

The antibody according to the present invention is an antibody that inhibits a result of an effect of coexistence of Myl with CD69, preferably an antibody that inhibits the result of the effect of coexistence of Myl9, Myl12a, or Myl12b with CD69, more preferably an antibody that inhibits the result of the effect of coexistence of Myl9, Myl12a, and Myl12b with CD69.

The antibody according to the present invention may be produced using Myl9, Myl12a, or Myl12b as an antigen. The antigen may be a full-length protein of any one of Myl9, Myl12a, and Myl12b or a partial peptide of the protein. The antigen is composed of at least 8 amino acids, preferably at least 10 amino acids, more preferably at least 12 amino acids, still more preferably 15 amino acids or more amino acids. In order to prepare a specific antibody, it is preferable to use a peptide containing a region consisting of a unique amino acid sequence in the antigen, that is, an epitope immunologically specific for the antigen. As a peptide preferably usable as the antigen, there may be given a peptide consisting of an amino acid sequence of SEQ ID NO: 24 in the sequence listing.

Such a full-length protein and a partial peptide of the protein may be produced as: cells in which a nucleic acid encoding the protein or peptide is expressed by a general genetic engineering technique (e.g., Sambrook J. et al. ed., Molecular Cloning: A Laboratory Manual (2d ed.) Cold Spring Harbor Laboratory Press, New York (1989), Ulmer, K. M., Science, 219: 666-671, 1983, and Ehrlich H. A. ed., PCR Technology. Principles and Applications for DNA Amplification. Stockton Press, New York (1989)); a cell-free synthesis product; or a chemical synthesis product. Alternatively, the full-length protein and partial peptide of the protein may be prepared from the cells or living organism-derived samples, or may be purified products thereof.

The antibody may be produced by utilizing an antibody production method well known. For example, the antibody is obtained by administering to an animal an antigen alone, or an antigen bound to a carrier, with or without an adjuvant, and thereby inducing immunity, such as a humoral immune response and/or a cellular immune response. The carrier is not particularly limited as long as the carrier itself does not exhibit any adverse action on the host, and is capable of enhancing antigenicity. Examples thereof may include cellulose, a polymerized amino acid, albumin, and keyhole limpet hemocyanin. Examples of the adjuvant may include Freund's complete adjuvant (FCA), Freund's incomplete adjuvant (FIA), Ribi (MPL), Ribi (TDM), Ribi (MPL+TDM), *Bordetella pertussis* vaccine, muramyl dipeptide (MDP), and an aluminum adjuvant (ALUM), and combinations thereof. As animals for immunization, Mouse, rat, rabbit, goat, horse or the like can be suitably used.

The antibody according to the present invention may be a monoclonal antibody or a polyclonal antibody. The polyclonal antibody may be acquired from the serum of an animal that was subjected to immunization by using any known method for recovering an antibody. As a preferred method for recovering an antibody, there is given an immunoaffinity chromatography method. The monoclonal antibody may be produced by using a known method such as a hybridoma method (Kohler and Milstein, Nature, 256:495, 1975). In the hybridoma method, a mouse, a hamster, or any other appropriate host animal is typically immunized with an antigen to induce lymphocytes producing an antibody that specifically binds with the antigen or being capable of producing the antibody. Alternatively, by using the lymphocytes producing the antibody or being capable of producing the antibody, hybridomas are produced by introducing means for transforming to immortal cells well known. For example, such lymphocytes are fused with the immortal cells by a method well known to produce hybridomas, followed by cloning the produced hybridomas and selecting a hybridoma producing an antibody of interest from the cloned hybridomas. The hybridoma is cultured and an antibody can be collected from the culture medium. The selection of the hybridoma may be performed, for example, by screening according to a known method (Harlow & Lane, Antibodies, A Laboratory Manual, Cold Spring Harbor Press, New York (1988), Goding, Monoclonal Antibodies, Principles and Practice (2d ed.) Academic Press, New York (1986)). That is, a desired hybridoma may be selected by testing specific immunoreactivity between a monoclonal antibody produced by the hybridoma and Myl, or inhibition of the result of the effect of coexistence of Myl with CD69.

A natural antibody structural unit typically includes a tetramer. Such a tetramer is composed of two homologous pairs of polypeptide chains (each pair has one full-length light chain (for example, about 25 kDa)) and one full-length heavy chain (for example, from about 50 kDa to about 70 kDa). The amino terminal part of each chain typically includes a variable region including about 100 amino acids to about 110 amino acids or more amino acids which is involved in antigen recognition. The carboxy terminal part of each chain typically defines a constant region that may be involved in an effector function. Human light chains are typically categorized into κ light chain and λ light chain. Heavy chains are typically categorized into μ, δ, γ, α, and ε, and antibody isotypes are defined as IgM, IgD, IgG, IgA, and IgE, respectively. IgG includes IgG1, IgG2, IgG3, and IgG4, and has several subclasses that are not limited thereto. IgM includes IgM1 and IgM2, and has subclasses that are not limited thereto. IgA also includes IgA1 and IgA2, and is subdivided into subclasses that are not limited thereto. In the light chains and the heavy chains, variable regions and constant regions are linked to each other with a J region including about 12 amino acids or more amino acids, and the heavy chains may also include a D region including about 10 amino acids or more amino acids (e.g., Paul, W., ed., Fundamental Immunology Ch. 7 (2nd ed.) Raven Press, N.Y. (1989)). Each variable region of a light chain/heavy chain pair typically forms an antigen-binding site.

The variable regions typically have the same overall structure including relatively conserved framework regions (FR) linked with three hypervariable regions (sometimes referred to as complementarity determining regions or CDRs). CDRs in two chains of each pair are typically aligned by the framework regions, which allows binding to a specific epitope. Both of a light chain variable region and a heavy chain variable region typically contain domains FR1, CDR1, FR2, CDR2, FR3, CDR3, and FR4 from the N-terminal to the C-terminal.

The antibody according to the present invention may be any of an intact antibody or an antibody fragment. The "intact antibody" means an antibody composed of a tetramer structural unit similar to that of a natural antibody. The "antibody fragment" means a fragment including a part of the intact antibody such as an antigen-binding region or a variable region of the intact antibody. Examples of the antibody fragment include a Fab fragment, a Fab1 fragment, a F(ab')₂ fragment, a Fv fragment, a diabody, a linear antibody (Zapata et al., Protein Eng. 8(10):1057-1062, 1995), a single-chain antibody molecule, and a multi-specific antibody composed from an antibody fragment. The "Fab fragment" is an antigen-binding fragment having a single antigen-binding site, which may be produced from one antibody by subjecting the antibody to papain digestion to obtain two identical Fab fragments each having a single antigen-binding site. The "F(ab')₂ fragment" is an antibody fragment that may be produced by subjecting an antibody to pepsin treatment, and is still capable of cross-linking antigens. The "Fv fragment" is an antibody fragment containing a complete antigen recognition site and antigen-binding site, and is composed of a dimer of one heavy chain variable domain and one light chain variable domain closely bound through a non-covalent bond. Half of the Fv containing only a single variable domain or antigen-specific three CDRs can recognize an antigen and can bind thereto. A "single-chain Fv" or "sFv" antibody fragment is the single-chain antibody molecule and has a feature of including a VH domain and VL domain of an antibody, in which these domains are present in a single polypeptide chain. A Fv polypeptide may further contain a polypeptide linker between the VH domain and the VL domain which allows sFv to form a desired structure for antigen binding (e.g., Rosenburg and Moore eds., Pluckthun in The Pharmacology of Monoclonal Antibodies, vol. 113, Springer-Verlag, New York, pp. 269-315 (1994)). The term "diabody" refers to a small antibody fragment having two antigen-binding sites, and this fragment includes a heavy chain variable domain (VH) linked to a light chain variable domain (VL) on the same polypeptide chain (Vn-VL) (e.g., EP 404097 B1, WO 93/11161 A1, and Hollinger et al., Proc. Natl. Acad. Sci. USA, 90:6444-6448, 1993). A short linker is used to make association between the two domains on the same chain. Thus, association between the domains and complementary domains on the other chain can be achieved to produce two antigen-binding sites.

The antibody according to the present invention may be produced as a chimeric antibody, or a partially humanized or completely humanized antibody. A non-human antibody may be humanized by any known method applicable in the art. The humanized antibody may be produced by using a transgenic animal in which the immune system is partially or completely humanized. The antibody according to the present invention or a fragment thereof may be partially or completely humanized. The chimeric antibody may be produced by any known technique in the art (e.g., U.S. Pat. Nos. 5,169,939 A, 5,750,078 A, 6,020,153 A, 6,420,113 B1, 6,423,511 B1, 6,632,927 B2, and 6,800,738 B1).

The antibody according to the present invention inhibits the result of the effect of coexistence of Myl with CD69, and hence is useful for elucidation, prevention, amelioration, and/or treatment of various diseases caused by functional abnormality of and quantitative abnormality of CD69, such as a CD69 activation caused by Myl.

The "CD69" is a type II transmembrane protein belonging to C-type rectin family. The amino acid sequence of CD69 and the nucleotide sequence of a nucleic acid encoding CD69 are well known to a person skilled in the art. A nucleic acid encoding human-derived CD69 may be, for example, DNA represented by the nucleotide sequence (NM_001781.2) of SEQ ID NO: 19. In addition, human-derived CD69 may be, for example, a polypeptide represented by the amino acid sequence (NP_001772.1) of SEQ ID NO: 20.

As the various diseases caused by functional abnormality of or quantitative abnormality of CD69, there may be preferably given inflammatory diseases. CD69 is constitutively expressed in platelets and is also expressed in activated neutrophils, eosinophils, or the like. Thus, CD69 is supposed to play a role in function expression of platelet and local inflammatory responses. In addition, it is revealed that CD69 on neutrophils plays a key role in development of arthritis (Non Patent Literature 5). Further, it has been reported that CD69 on CD4 T cells controls an allergic airway inflammation and the antibody against CD69 suppresses the allergic airway inflammation (Non Patent Literature 6).

The term "inflammatory disease" means a disease accompanied with an inflammatory condition. The inflammatory condition means a general or partial serial biological defense reaction against various injury factors acting on a biological body, for example, a pathological condition, such as a histological disorder or a circulatory disorder caused by a change in number of cells of the immune system, a change in migration speed of the cells, and a change in activity of the cells. Examples of the cells of immune system may include T cells, B cells, monocytes or macrophages, antigen-presenting cells (APCs), dendritic cells, microglia, NK cells, NKT cells, neutrophils, eosinophils, mast cells, and any other cells which are specifically related with immunity, such as cytokine-producing endothelial cells or cytokine-producing epithelial cells.

The inflammatory disease is not particularly limited as long as the disease is accompanied with an inflammatory condition, and preferred examples thereof may include an airway inflammation, such as an allergic airway inflammation, and an autoimmune disease. More specific examples thereof may include asthma, atopic dermatitis, inflammatory bowel disease, and arthritis.

The term "treatment" means performing a certain procedure to relieve or reduce a disease or a symptom thereof, or to arrest its progression. The "treatment" may include the prevention of development of the disease.

The antibody according to the present invention may be produced as a pharmaceutical composition containing a pharmaceutically acceptable carrier (pharmaceutical carrier), as required.

The pharmaceutical carrier may be exemplified by a filler, an expander, a binder, a moisture imparting agent, a disintegrant, a lubricant, a diluent, and an excipient, which are generally used depending on the form of use of a formulation. Those carriers are appropriately selected and used depending on the administration form of a formulation to be obtained. The pharmaceutical carrier may be more specifically exemplified by water, a pharmaceutically acceptable organic solvent, collagen, polyvinyl alcohol, polyvinylpyrrolidone, a carboxyvinyl polymer, sodium alginate, water-soluble dextran, sodium carboxymethylstarch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, and lactose. One kind of those carriers may be appropriately used, or two or more kinds thereof may be appropriately used in combination depending on the dosage form of a drug of interest. In addition, for example, a stabilizer, a microbicide, a buffering agent, an isotonizing agent, a chelating agent, a surfactant, and a pH regulator may be appropriately used. The stabilizer may be exemplified by human serum albumin and a typical L-amino acid, sugar, and cellulose derivative. The L-amino acid is not particularly limited, and for example, any of glycine, cysteine, and glutamic acid may be used. In addition, the sugar is not particularly limited, and for example, any of the following sugars may be used: monosaccharides, such as glucose, mannose, galactose, and fructose; sugar alcohols, such as mannitol, inositol, and xylitol; disaccharides, such as sucrose, maltose, and lactose; polysaccharides, such as dextran, hydroxypropylstarch, chondroitin sulfate, and hyaluronic acid; and derivatives thereof. In addition, the cellulose derivative is not particularly limited, and for example, any of the following derivatives may be used: methylcellulose, ethylcellulose, hydroxyethylcellulose, hydroxypropylcellulose, hydroxypropylmethylcellulose, and sodium carboxymethylcellulose. In addition, the surfactant is not particularly limited, and for example, any of an ionic surfactant and a nonionic surfactant may be used. The surfactant encompasses, for example, polyoxyethylene glycol sorbitan alkyl ester-based, polyoxyethylene alkyl ether-based, sorbitan monoacyl ester-based, and fatty acid glyceride-based surfactants. The buffering agent may be exemplified by boric acid, phosphoric acid, acetic acid, citric acid, s-aminocaproic acid, glutamic acid, and/or salts corresponding thereto (such as alkali metal salts and alkaline earth metal salts thereof, e.g., a sodium salt, a potassium salt, a calcium salt, and a magnesium salt thereof). The isotonizing agent may be exemplified by sodium chloride, potassium chloride, a sugar, and glycerin. The chelating agent may be exemplified by sodium edetate and citric acid.

The antibody according to the present invention may be used in combination with one or more known anti-inflammatory disease drugs for treating inflammatory diseases.

The pharmaceutical composition including the antibody according to the present invention may include the antibody and an additional active ingredient effective in treating an inflammatory disease in combination.

The dose range of the pharmaceutical composition is not particularly limited and is appropriately selected depending on efficacy of a component contained, a dosage form, an administration route, types of diseases, characteristics of a subject (body weight, age, disease condition, with or without use of other pharmaceuticals), physician's discretion, or the like. In general, it is preferred that an appropriate dose fall within the range of, for example, from about 0.01 µg to about 100 mg, preferably from about 0.1 µg to about 1 mg per kg of body weight of the subject. However, those doses may be changed through a general routine experiment for optimization well known in the art. The dosage may be administered in one to several divided portions a day and may be intermittently administered once every several days or several weeks.

When administering the pharmaceutical composition according to the present invention, the pharmaceutical composition may be used alone or used together with any other compounds or pharmaceuticals necessary for treatment.

In terms of a route of administration, any of systemic administration and local administration may be selected. In this case, an appropriate administration route is selected depending on diseases, symptoms, or the like. The drug according to the present invention may be administered by any of an oral route and a parenteral route, more preferably an oral route. Examples of the parenteral route may include subcutaneous administration, intradermal administration, and intramuscular administration as well as general intravenous administration and intraarterial administration.

In terms of a dosage form, it is not particularly limited and various dosage forms may be adopted. For example, the pharmaceutical composition may be used as a solution formulation. In addition, the solution formulation may be lyophilized so that the formulation can be preserved and then dissolved with a buffer containing water, physiological saline, or the like to prepare a formulation having an appropriate concentration before use. The dosage form may be a prolonged dosage form or a sustained-release dosage form.

Specific examples of the dosage form for oral administration may include a tablet, a capsule, a powder, a granule, a pill, a liquid, an emulsion, a suspension, a solution, a spirit, a syrup, an extract, and an elixir. Specific examples of the dosage form for parenteral administration may include, but are not limited to, injections, such as a subcutaneous injection, an intravenous injection, an intramuscular injection, and an intraperitoneal injection, a transdermal absorption formulation or a patch, anointment or a lotion, a sublingual agent for buccal administration, an oral patch, an aerosol for transnasal administration, and a suppository. Those formulations may be produced by a known method commonly used in a formulation step.

When a solid formulation for oral administration is prepared, an excipient and a binder, a disintegrant, a lubricant, a colorant, a taste masking agent, an odor masking agent, or the like, as required, are added to the active ingredient described above, and then a tablet, a coated tablet, a granule, a powder, a capsule, or the like may be produced from the mixture by an ordinary method. Such additive may be an additive generally used in the art. Examples of the excipient may include lactose, saccharose, sodium chloride, dextrose, starch, calcium carbonate, kaolin, microcrystalline cellulose, and silicic acid. Examples of the binder may include water, ethanol, propanol, simple syrup, dextrose liquid, starch liquid, gelatin liquid, carboxymethylcellulose, hydroxypropylcellulose, hydroxypropylstarch, methylcellulose, ethylcellulose, shellac, calcium phosphate, and polyvinylpyrrolidone. Examples of the disintegrant may include dry starch, sodium alginate, agar powder, sodium hydrogen carbonate, calcium carbonate, sodium laurylsulfate, stearic acid monoglyceride, and lactose. Examples of the lubricant may include purified talc, a stearic acid salt, borax, and polyethylene glycol. Examples of the taste masking agent may include saccharose, bitter orange peel, citric acid, and tartaric acid.

When a liquid formulation for oral administration is prepared, a taste masking agent, a buffering agent, a stabilizer, an odor masking agent, or the like is added to the compound described above, and then an oral liquid, a syrup, an elixir, or the like may be produced from the mixture by an ordinary method. The taste masking agent in this case may be the taste masking agent exemplified above. An example of the buffering agent may be sodium citrate. Examples of the stabilizer may include tragacanth, gum arabic, and gelatin.

When the injection is prepared, a pH regulator, a buffering agent, a stabilizer, an isotonizing agent, a local anesthetic, or the like is added to the compound described above, and then subcutaneous, intramuscular, and intravenous injections may be produced from the mixture by an ordinary method. Examples of the pH regulator and the buffering agent in this case may include sodium citrate, sodium acetate, and sodium phosphate. Examples of the stabilizer may include sodium pyrosulfite, ethylenediaminetetraacetic acid (EDTA), thioglycolic acid, and thiolactic acid. Examples of the local anesthetic may include procaine hydrochloride and lidocaine hydrochloride. Examples of the isotonizing agent may include sodium chloride and dextrose.

The method of identifying a compound that inhibits a result of an effect of coexistence of Myl with CD69 may be performed by allowing Myl and CD69 to coexist in presence of a test compound, subsequently measuring an effect of coexistence of Myl and CD69, and selecting a compound that inhibits the effect.

The method of identifying a compound that inhibits a result of an effect of coexistence of Myl with CD69 may also be performed by, for example, allowing Myl and CD69 to coexist in presence of a test compound, subsequently measuring binding of Myl with CD69, and selecting a compound that inhibits the binding.

The method of identifying a compound that inhibits a result of an effect of coexistence of Myl with CD69 may also be performed by using, in place of Myl, a peptide of the N-terminal region in the amino acid sequence of Myl where Myl supposedly acts on CD69, for example, a peptide of the region represented by the amino acid sequence of SEQ ID NO: 24 in the sequence listing.

The method of identifying a compound that inhibits a result of an effect of coexistence of Myl with CD69 preferably includes the following steps (i) to (iii):

(i) bringing Myl into contact with a test compound;
(ii) allowing Myl and CD69 to coexist; and
(iii) measuring an effect of coexistence of Myl with CD69.

In the step (i), Myl may be brought into contact with the test compound either in the absence or presence of CD69, more preferably in the absence of CD69, because in the absence of CD69, the test compound may be identified which acts on Myl to inhibit a result of an effect of coexistence of Myl with CD69.

The effect of the test compound on the effect of coexistence of Myl with CD69 may be determined using the results obtained by measuring the effect of coexistence of Myl with CD69 and comparing the results in the case where Myl is brought into contact with the test compound with the results in the case where Myl is not brought into contact with the test compound. When the effect of coexistence of Myl with CD69 is decreased in the case where Myl is brought into contact with the test compound compared to the case where Myl is not brought into contact with the test compound, the test compound can be determined to inhibit the effect of coexistence of Myl with CD69.

Measurement of the effect of coexistence of Myl with CD69 may be performed using various analysis methods which are used in common screening systems for pharmaceuticals. For example, the measurement is performed by selecting a condition in which the effect of coexistence of Myl with CD69 can be exhibited, allowing Myl and CD69 to coexist under the condition, and detecting the effect of coexistence of Myl with CD69. The condition that allows the coexistence of Myl and CD69 may be an in vitro condition or an in vivo condition, preferably an in vitro condition. Myl and CD69 may be produced as a cell in which Myl and CD69 is expressed using a known method, such as a general genetic engineering technique, a cell-free synthesis product, or a chemical synthesis product. Alternatively, Myl and CD69 may be products prepared from such cells or a biological sample and may be products further purified from the prepared products.

For example, when measuring the binding of Myl with CD69, the measurement may be performed by separating a complex that is formed by binding of Myl and CD69 from free Myl and free CD69, which are not bound with each other, and detecting the complex by a known method, such as immunoblotting. Alternatively, the binding may be measured by performing a binding reaction between Myl and CD69 and then measuring Myl bound with CD69 by using an antibody against Myl. The antibody bound to Myl may be detected using a secondary antibody labeled with a marker substance. The binding may also be detected using an antibody previously labeled with a marker substance. Alternatively, the binding may be detected by previously labeling Myl for use in the binding reaction with CD69 with a desired marker substance, performing the identification method, and detecting the marker substance. As the marker substance, any substance used in a general binding analysis method may be utilized and examples thereof may include tag peptides, such as glutathione S-transferase (GST), His-tag, Myc-tag, HA-tag, FLAG-tag, and Xpress-tag, a fluorochrome, enzymes, such as horseradish peroxidase (HRP) and alkaline phosphatase (ALP), and biotin. Conveniently, a radioisotope may be utilized. The detection of the marker substance may be performed by a detection method well known.

Alternatively, the binding of Myl and CD69 may be measured with a surface plasmon resonance sensor, such as BIACORE system, a scintillation proximity assay (SPA), or an application method of fluorescence resonance energy transfer (FRET).

The compound identified by the method of identifying a compound that inhibits a result of an effect of coexistence of Myl with CD69 may serve as an active ingredient of a composition for treating an inflammatory disease. That is, there can be provided a candidate compound serving as an active ingredient of a composition for treating an inflammatory disease by selecting such a compound through the use of the method of identifying a compound that inhibits a result of an effect of coexistence of Myl with CD69 according to the present invention.

Now, the present invention is described in more detail by way of Examples. However, the scope of the present invention is not limited to the following Examples.

EXAMPLES

Example 1

Screening for a molecule acting on CD69 to allow CD69 to express the function was performed. Specifically, screening for a protein that binds to CD69 was performed. Firstly, a CD69 protein was obtained by a genetic engineering technique and purified.

Specifically, at first, mouse CD69 protein (hereinafter abbreviated as mCD69) was purified. mCD69 extracellular domain (Extra Cellular Domain: positions 188 to 600 starting from transcription initiation site: hereinafter sometimes abbreviated as EC) sequence prepared from mouse spleen cDNA by a PCR was inserted into a multi-cloning site of pET42a (TAKARA BIO INC.) having glutathione S-transferase (hereinafter abbreviated as GST) tag incorporated on the N-terminal side to produce an *E. coli* mCD69 EC-expression vector, pET42a GST-mCD69EC. A product obtained by transforming pET42a GST-mCD69EC to an *E. coli* BL21 (DE3) strain was subjected to the induction of protein expression using isopropyl β-D-1-thiogalactopyranoside (hereinafter abbreviated as IPTG; manufactured by Sigma-Aldrich Co. LLC.) The expressed GST-mCD69EC protein was subjected to the following refolding process because the protein was contained in an insoluble fraction and had no correct conformation. The insoluble fraction was solubilized with a denaturing buffer (20 mM Tris-HCl, 500 mM NaCl, 6 M guanidine hydrochloride, and 10 mM imidazole (pH 8.0)) while the cells were disrupted by using a sonicator (Microson Ultrasonic Disruptor: MISONIX). All purification processes were carried out by using AKTAprime plus (GE Healthcare) with a gradient flow rate. Further, buffer exchange was carried out with a refolding buffer (20 mM Tris-HCl, 500 mM NaCl, 6 M urea, 10 mM imidazole (pH 8.0)), and then treatment with washing-buffer (20 mM Tris-HCl (pH 8.0), 500 mM NaCl, 10 mM imidazole) and elution-buffer (20 mM Tris-HCl (pH 8.0), 500 mM NaCl, 500 mM imidazole) was carried out. After that, buffer exchange was carried out with a phosphate buffered saline (hereinafter abbreviated as PBS) by using a dialysis membrane (GE Healthcare). Thus, the GST-mCD69EC protein was obtained. A GST protein denatured and refolded in the same manner as the GST-mCD69EC protein was used as a control protein.

Then, a bone marrow extract in which a protein binding to CD69 was supposedly contained (hereinafter abbreviated as BM lysate) was prepared. It has been reported that CD69 is involved in the migration of memory CD4 T cells to bone marrow (Non Patent Literature 4), indicating that a molecule acting on CD69 to modulate the function of CD69 is present in bone marrow. Specifically, the bone marrow in mouse femur was treated with collagenase IV (Sigma-Aldrich Co. LLC.), and then the bone marrow was lysed in a lysis buffer containing a protease inhibitor (Roche Diagnostics K.K.) (20 mM Tris-HCl (pH 8.0), 150 mM NaCl, 0.05% NaN$_3$, 10% glycerol, 1% Triton-X100™ to prepare a bone marrow extract.

The bone marrow extract obtained was mixed with the purified GST-mCD69EC protein and subjected to immunoprecipitation using anti-GST antibody (Wako Pure Chemical Industries, Ltd.) and protein-G (GE Healthcare). The precipitate was separated by sodium dodecylsulfate polyacrylamide gel electrophoresis (SDS-PAGE), and then the separated proteins were stained with Coomassie Brilliant Blue (hereinafter abbreviated as CBB) using Bio-Safe CBB G-250 stain (Bio-Rad Laboratories, Inc.)

As shown in FIG. 1A, a specific band indicating a protein binding to the GST-mCD69EC protein was detected. The band was cut out and the cut band was subjected to LC-MS/MS analysis to identify the protein binding to the GST-mCD69EC protein. Consequently, it was revealed that the protein binding to the GST-mCD69EC protein was Myl9 having the amino acid sequence indicated with bold lines in FIG. 1B, or Myl12a and Myl12b each having high homology with Myl9.

Then, whether the binding of Myl9, Myl12a, and Myl12b with CD69 actually occurred was investigated. Firstly, mCD69EC sequence was inserted to p3×FLAG CMV-9 (Sigma-Aldrich Co. LLC.) having Flag tag incorporated at the N-terminal to produce an expression vector of mCD69EC sequence having Flag-Tag added at the N-terminal. The expression vector was transformed to 293 T cells to overexpress 3×Flag mCD69EC, and then a cell extract was prepared. As a control, a cell extract was prepared from 293 T cells overexpressing 3×Flag peptide. 3×Flag mCD69EC protein or 3×Flag peptide was purified from the cell extract using anti-DYKDDDDK (SEQ ID NO: 21) tag antibody beads (Wako Pure Chemical Industries, Ltd.). In this case, DYKDDDDK is a peptide represented by a single letter code for an amino acid. Those purified proteins were each subjected to a reaction with a bone marrow extract (BM lysate) in the same manner as described above and the resultant products were subjected to immunoprecipitation using anti-Flag M2 antibody (Sigma-Aldrich Co. LLC.) and protein-G (GE Healthcare). After the immunoprecipitation was performed, the precipitates were separated by SDS-PAGE and transferred to a polyvinylidene difluoride (PVDF) membrane (Bio-Rad Laboratories, Inc.). Subsequently, immunoblotting was performed using an antibody which recognized Myl9, Myl12a, and Myl12b (hereinafter referred to as anti-Myl9/12 antibody). That is, each protein was detected by ChemiDocXRS+ (Bio-RadLaboratories, Inc.) with ECL detection reagents (GE Healthcare) using rabbit anti-Myl9 antibody (Abcam plc.) as a primary antibody and horseradish peroxidase (HRP)-labeled anti-rabbit IgG antibody (Cell Signaling Technology, Inc.) as a secondary antibody. Deglycosylation treatment of the mCD69EC protein was performed by adding 500 U of N-glycosidase PNGase F (New England Biolabs Ltd.) to 1 μg of 3×FLAG mCD69EC.

Figure 1C:
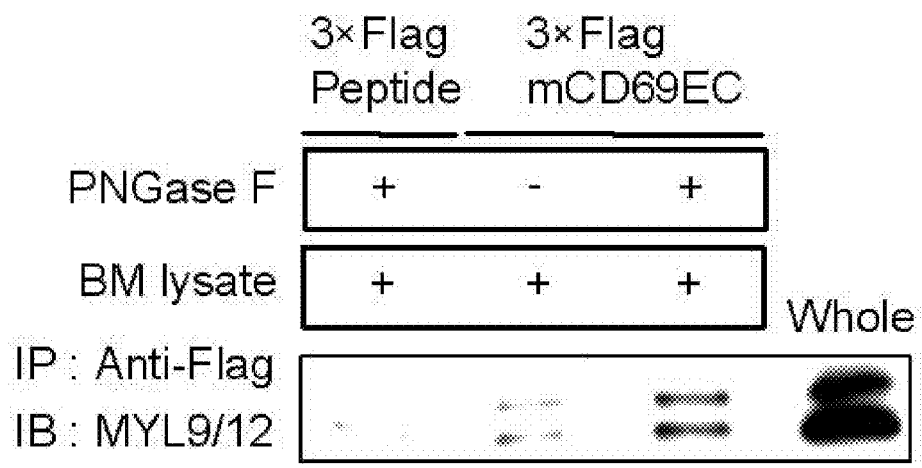
FIG. 1C is an image for showing that mouse CD69 extracellular domain protein having 3×Flag-tag added thereto (3×Flag mCD69EC) was subjected to a reaction with a bone marrow extract and the resultant mixture was subjected to immunoprecipitation using anti-Flag M2 antibody and immunoblotting using anti-Myl9/12 antibody, and a band indicating an interaction between 3×Flag mCD69EC and Myl9/12 was detected. Meanwhile, a band indicating an interaction between 3×Flag peptide and Myl9/12 was not found. In addition, the interaction between 3×Flag mCD69EC and Myl9/12 was enhanced in the case of treatment with a deglycosylation enzyme, PNGase F.

Consequently, a band indicating the binding of the 3×Flag mCD69EC protein immunoprecipitated using the anti-Flag M2 antibody with the anti-Myl9/12 antibody was observed (FIG. 10). Meanwhile, in the 3×Flag peptide immunoprecipitated using the anti-Flag M2 antibody, a band indicating the binding with the anti-Myl9/12 antibody was not observed. Those results indicate the binding of the mCD69EC protein with Myl9, Myl12a, and Myl12b, which are recognized by the anti-Flag M2 antibody. In addition, the binding was enhanced in the case where CD69EC was previously treated with PNGase F, a deglycosylation enzyme (FIG. 1C).

From those results, it is revealed that Myl9, Myl12a, and Myl12b, which proteins are contained in the bone marrow extract, bind with CD69. In addition, it is proved that the binding of Myl9, Myl12a, and Myl12b with CD69 is enhanced by treatment with a deglycosylation enzyme.

Example 2

It has been reported that memory CD4 T cells migrate to bone marrow through contact with CD69, and hence the function of CD69 in vivo was analyzed. In addition, a change in glycosylation state of CD69 on CD4 T cells in association with the activation of the cells was analyzed.

Firstly, the molecular weight of CD69 protein treated with a glycosylation inhibitor, tunicamycin, was measured. pFLAG-CMV mCD69FL, which was produced by incorporating the full-length sequence of mouse CD69 gene (hereinafter sometimes abbreviated as mCD69FL) into a FLAG vector, was overexpressed in 293 T cells using FuGENE HD Transfection (Promega KK.) and the cells were treated with 10 mg/ml of tunicamycin for the last 24 hours before the collection of the cells. The collected cells were lysed with a protease inhibitor (Roche Diagnostics K.K.)-containing lysis buffer (20 mM Tris-HCl (pH 8.0), 150 mM NaCl, 0.05% $NaN_3$, 10% glycerol, 1% Triton-X100™) and the obtained cell extract was separated by SDS-PAGE and transferred to a PVDF membrane (Bio-Rad Laboratories, Inc.) Immunoblotting was performed using rabbit anti-Flag M2 antibody (Sigma-Aldrich Co. LLC.) as a primary antibody and HRP-labeled anti-rabbit IgG antibody (Cell Signaling Technology, Inc.) as a secondary antibody. Proteins were detected by ChemiDocXRS+(Bio-Rad Laboratories, Inc.) with ECL detection reagents (GE Healthcare).

Figure 2A:
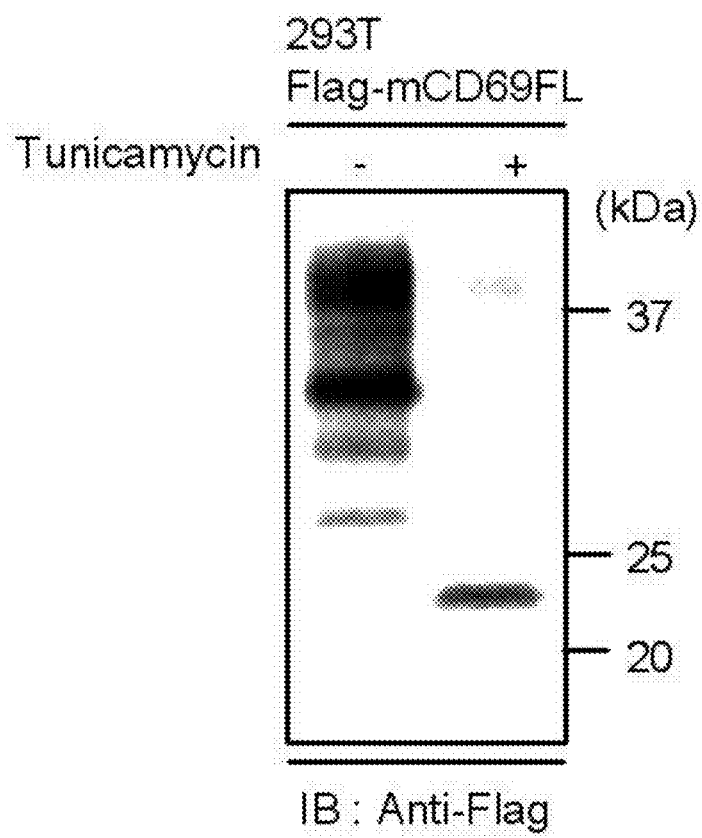
FIG. 2A is an image for showing that when 293 T cells expressing a mouse full-length CD69 protein having Flag-tag added thereto (Flag-mCD69FL) were treated with a glycosylation inhibitor, tunicamycin (Tunicamycin), the molecular weight of Flag-mCD69FL contained in the extract of the cells was decreased compared to that of non-treated cells.

As shown in FIG. 2A, CD69FL which was overexpressed in the 293 T cells showed bands at around 35 kDa, while when the cells were treated with tunicamycin, a band of CD69FL having a small molecular weight appeared.

Then, CD69 was detected by immunoblotting in order to determine the molecular weight of CD69 protein which was expressed in CD4 T cells. Firstly, Th2 cells were induced to differentiate from CD4 T cells and CD69FL having FLAG-tag added thereto was introduced to the Th2 cells using a retroviral vector. The resultant Th2 cells were subjected to immunoprecipitation using anti-FLAG antibody and immunoblotting using anti-FLAG antibody to examine change in glycosylation state of CD69 in association with the activation of the Th2 cells. A retrovirus was produced by introducing pMXs-IRES GFP (IG)-Mock (empty) vector or pMXs-IG-FLAG CMV2 mCD69FL vector to Plat E cells. CD4 T cells were isolated from C57BL/6 mouse spleen cells using fluorescein isothiocyanate (FITC)-labeled anti-CD4 antibody (BD Pharmingen) and anti-FITC microbeads (Miltenyi Biotec). Under the condition for differentiation to Th2 cells (in the presence of 25 U/ml interleukin-2 (IL-2), 100 U/ml IL-4, and anti-interferon γ (IFNγ) neutralizing antibody), the CD4 T cells were induced to differentiate to Th2 cells by stimulation with solid-phased anti-T cell receptor (TCR) β antibody (H57) and anti-CD28 antibody (BioLegend). On Day 2, the cells were infected with a retrovirus produced using solid-phased RetroNectin. On Day 5, the cells were collected and cultured in a culture medium for 1 day and the cultured cells were used as resting cells. In addition, the cells collected on Day 5 were cultured in a culture medium for 2 days and the cultured cells were stimulated with the solid-phased anti-TCR β antibody for 24 hours and then used in the experiment. A cell extract was prepared by the same treatment as the method described above and the prepared cells were subjected to immunoprecipitation using rabbit anti-Flag M2 antibody and protein-G (GE Healthcare). The precipitates were separated by SDS-PAGE and transferred to a PVDF membrane (Bio-Rad Laboratories, Inc.). Immunoblotting was performed using the same antibody as described above to detect proteins.

Figure 2B:
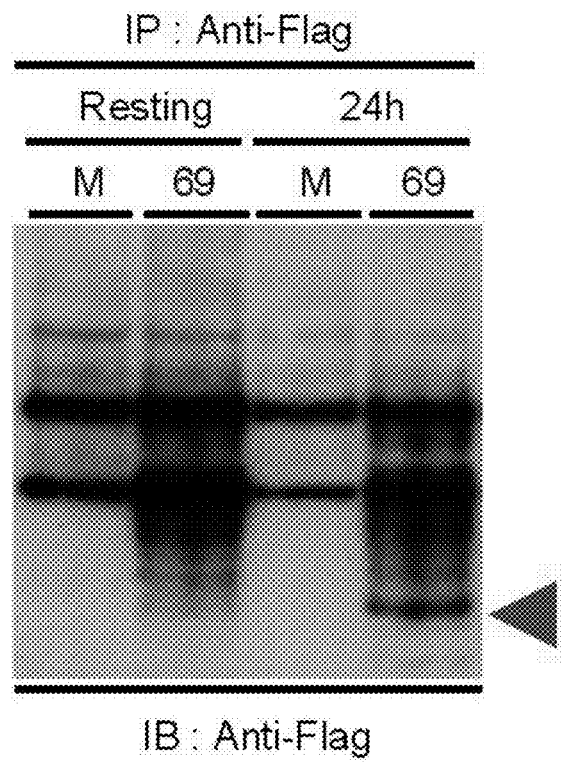
FIG. 2B is an image for showing that when Th2 cells which were induced to differentiate from mouse CD4 T cells and to which Flag-mCD69FL was introduced were stimulated with anti-T cell receptor (TCR) β antibody for 24 hours, a part of a Flag-mCD69FL molecule having a small molecular weight, which was estimated to undergo no glycosylation, was detected (arrow).

As shown in FIG. 2B, the expression of CD69 having a small molecular weight, which was estimated to undergo no glycosylation, was observed in the activated Th2 cells which were stimulated with the anti-TCR β antibody (FIG. 2B, the right lane) compared to the Th2 cells which were not stimulated (FIG. 2B, the second lane from the left).

The migration of the CD4 T cells to bone marrow 24 hours and 48 hours after the stimulation was observed in order to examine a relationship between the change in glycosylation state of CD69 on the CD4 T cells and the function. The CD4 T cells were isolated from the mouse spleen expressing Thy1.1, a T cell surface marker molecule, through the use of biotin-labeled anti-CD4 Fab antibody and streptavidin microbeads (Miltenyi Biotec) and the isolated cells were stimulated using solid-phased anti-CD3s antibody (eBioscience) and anti-CD28 antibody. The cells were collected 24 hours or 48 hours after the stimulation and the collected cells were transferred into a mouse expressing Ly5.1, a pan-leukocyte surface molecule, by tail vein injection, and 1 hour after the transfer, detection of Thy1.1$^+$CD4$^+$ cells in the bone marrow and spleen was carried out. FITC-labeled Ly5.1 antibody, phycoerythrin-cyanin 7 (hereinafter abbreviated as PE-Cy7)-labeled CD4 antibody, allophycocyanin-cyanin 7 (hereinafter abbreviated as APC-Cy7)-labeled B220 antibody, and PB-labeled Thy1.1 antibody were used for the detection. The capacity of migration of the CD4 T cells to bone marrow was indicated by a ratio obtained by dividing the number of cells transferred to bone marrow by the number of cells transferred to spleen.

Figure 2C:
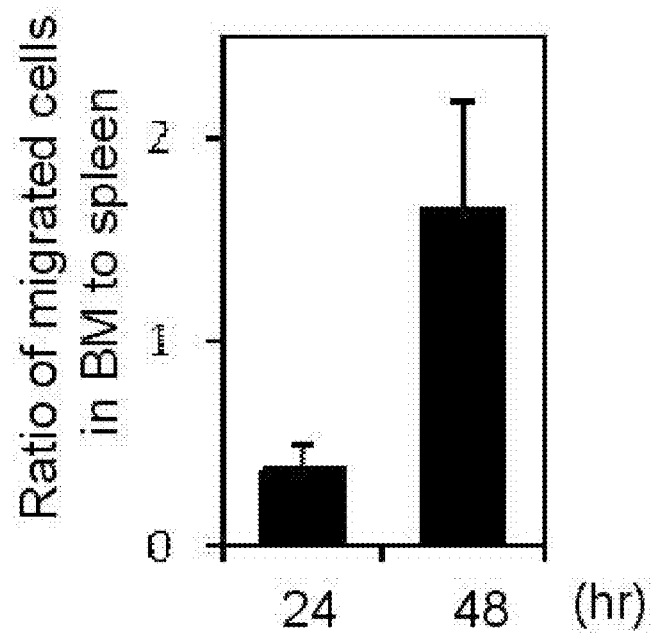
FIG. 2C is a graph for showing that when mouse CD4 T cells were stimulated with anti-CD3ε antibody and anti-CD28 antibody which were then transferred into a mouse 24 hours after the stimulation, the migration of the cells to bone marrow was found, and the migration to bone marrow was further enhanced 48 hours after the stimulation. The vertical axis represents a ratio obtained by the number of cells transferred to bone marrow by the number of cells transferred to spleen (Example 2).

As shown in FIG. 2C, the migration of the Thy1.1$^+$CD4$^+$ cells to bone marrow was found from 48 hours after the stimulation.

From those results and the results of Example 1, it can be considered that the stimulated CD4 T cells express CD69 with less glycosylation and migrate to bone marrow through binding with Myl9, Myl12a, or Myl12b.

It was investigated whether the binding of Myl9, Myl12a, and Myl12b with CD69 was involved in the migration of the stimulated CD4 T cells to bone marrow. Specifically, according to the same method as described above, Thy1.1$^+$CD4 T cells isolated from mouse spleen were stimulated with the solid-phased anti-CD3ε antibody and collected after 8 hours, and then the collected cells were transferred into a C57BL/6 mouse expressing Thy1.2, a T cell surface molecule. 1 hour before the transfer of the cells, anti-Myl9/12 antibody (MEDICAL & BIOLOGICAL LABORATORIES CO., LTD) or rabbit IgG antibody (Jackson ImmunoResearch Labs, Inc.), a control antibody was intraperitoneally administered to mice, and 1 hour after the transfer, detection of Thy1.1$^+$CD4$^+$ cells in bone marrow and peripheral blood were carried out by the same method as described above and a ratio of Thy1.1, CD4 double-positive cells was calculated. In addition, the capacity of migration of the CD4 T cells to bone marrow was indicated by a ratio obtained by dividing the number of cells transferred to bone marrow by the number of cells transferred to peripheral blood.

Figure 2D:
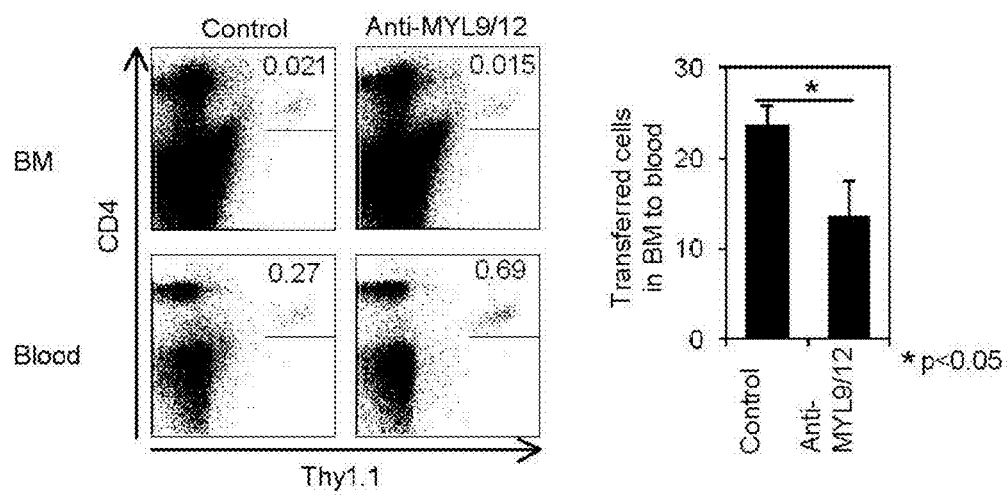
FIG. 2D includes an image and graph for showing that when mouse Thy1.1$^+$CD4 T cells were stimulated with anti-CD3ε antibody which were then transferred into a mouse 8 hours after the stimulation, the migration of the transferred cells, that is to say Thy1.1$^+$CD4 T cells, to bone marrow was decreased by pre-administration of anti-Myl9/12 antibody compared to a mouse given a control rabbit IgG antibody. The vertical axis of the right panel represents a ratio obtained by dividing the number of cells transferred to bone marrow by the number of cells transferred to peripheral blood.

As shown in the right panel of FIG. 2D, the ratio of Thy1.1$^+$CD4$^+$ cells which migrated to bone marrow to Thy1.1$^+$CD4$^+$ cells in blood (cells which did not migrate to bone marrow) was decreased in the anti-Myl9/12 antibody administration group compared to the control group. That is, it is proved that the migration of the CD4 T cells to bone marrow is inhibited by inhibiting the effect of coexistence of Myl9 or Myl12 and CD69. Consequently, it is suggested that the interaction between Myl9, Myl12a, or Myl12b and CD69 leads to efficient migration of the CD4 T cells to bone marrow.

From those results and the results of Example 1, it is suggested that when the CD4 T cells 24 hours to 48 hours after the antigen stimulation expresses CD69 which does not undergo glycosylation, CD69 binds with Myl9, Myl12a, or Myl12b, and the cells efficiently migrate to bone marrow.

Example 3

Identification of cells expressing Myl9, Myl12a, or Myl12b was carried out, because it was suggested that the binding of Myl9, Myl12a, or Myl12b in bone marrow with CD69 led to the migration of the CD4 T cells to bone marrow.

Firstly, tissue sections of organs in a mouse were subjected to immunostaining using anti-Myl9/12 antibody to identify cells expressing Myl9, Myl12a, or Myl12b. Specifically, femur, spleen, thymus gland, and mesenteric lymph node in a mouse were fixed with 4% paraformaldehyde, followed by replacement with 30% sucrose. The prepared frozen sections of the organs were stained using anti-Myl9/12 antibody and Alexa 488-labeled anti-rabbit IgG antibody. A staining procedure was performed in accordance with the instruction and histological analysis was performed with a confocal laser microscope (LSM710, manufactured by Carl Zeiss).

Figure 3A:
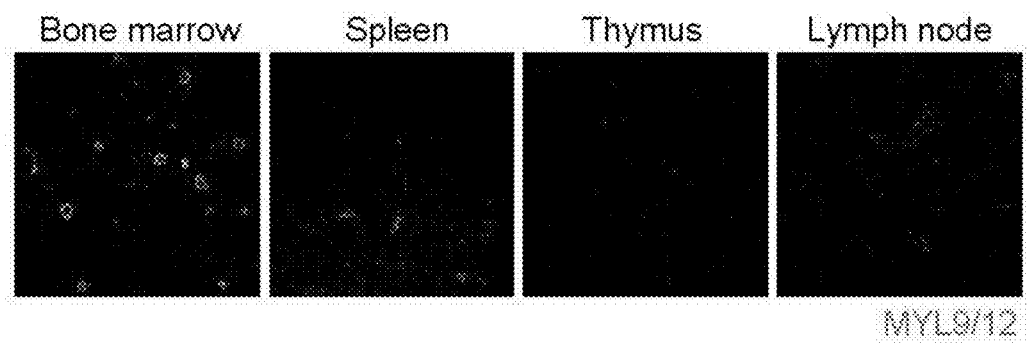
FIG. 3A is an image for showing that a large number of cells expressing Myl9, Myl12a, or Myl12b were found in bone marrow and the cells were also slightly found in spleen. Analyses of the cells expressing Myl9, Myl12a, or Myl12b were performed for organs of a mouse, that is, tissue sections of bone marrow of femur (Bone marrow), spleen (Spleen), thymus gland (Thymus), and mesenteric lymph node (Lymph node) by immunostaining using anti-Myl9/12 antibody (Example 3).

As shown in FIG. 3A, it was found that cells expressing the protein which was recognized by the anti-Myl9/12 antibody, that is, Myl9, Myl12a, or Myl12b are present in bone marrow. In addition, the protein was slightly found in spleen.

Then, a tissue extract was prepared from each of mouse organs, that is, bone marrow of femur, spleen, thymus gland, and mesenteric lymph node in a mouse and the expression level of Myl9, Myl12a, or Myl12b was investigated by immunoblotting using the anti-Myl9/12 antibody. Specifically, bone marrow of femur, spleen, thymus gland, and mesenteric lymph node in a mouse were lysed in a protease inhibitor (Roche Diagnostics K.K.)-containing lysis buffer (20 mM Tris-HCl (pH 8.0), 150 mM NaCl, 0.05% NaN$_3$, 10% glycerol, 1% Triton-X100™). The bone marrow was used after treatment with collagenase IV (Sigma-Aldrich Co. LLC.) before the lysis. The obtained tissue extracts were separated by SDS-PAGE and then transferred to a PVDF membrane (Bio-Rad Laboratories, Inc.) Rabbit anti-Myl9 antibody (Abcam plc.) and mouse anti-α-tubulin antibody (NeoMarkers) were used as primary antibodies. Anti-rabbit IgG antibody (Cell Signaling Technology, Inc.) and anti-mouse IgG antibody (GE Healthcare) each labeled with HRP were used as secondary antibodies. Proteins were detected by ChemiDocXRS+(Bio-Rad Laboratories, Inc.) with ECL-detection reagents (GE Healthcare).

Figure 3B:
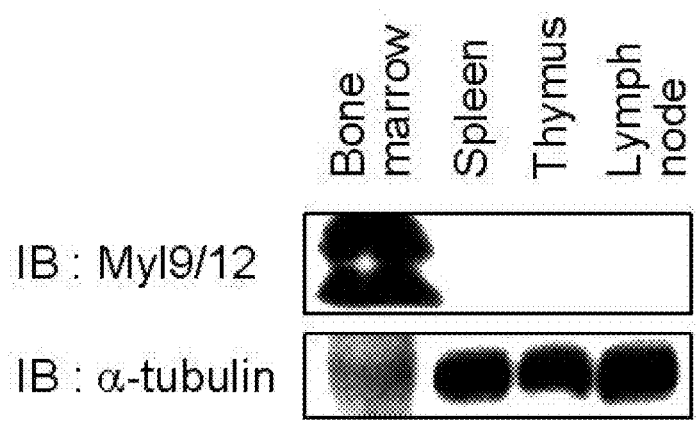
FIG. 3B is an image for showing that the expression level of Myl9, Myl12a, or Myl12b was high in bone marrow. Analyses of expression levels of the proteins were performed for organs of a mouse, that is, tissue extracts were prepared from bone marrow of femur (Bone marrow), spleen (Spleen), thymus gland (Thymus), and mesenteric lymph node (Lymph node) and the extracts were analyzed by immunoblotting using anti-Myl9/12 antibody. As a control, α-tublin in each of the tissue extracts was detected in the same manner as described above.

As shown in FIG. 3B, in the bone marrow cell extract, a high expression level of the protein which was recognized by the anti-Myl9/12 antibody, that is, Myl9, Myl12a, or Myl12b was found.

In addition, Myl9, Myl12a, or Myl12b-expressing cells present in bone marrow were examined by immunostaining for analysis. Specifically, bone marrow tissue sections were treated in the same manner as described above and then analyzed by immunostaining using a fluorochrome.

Figure 3C:
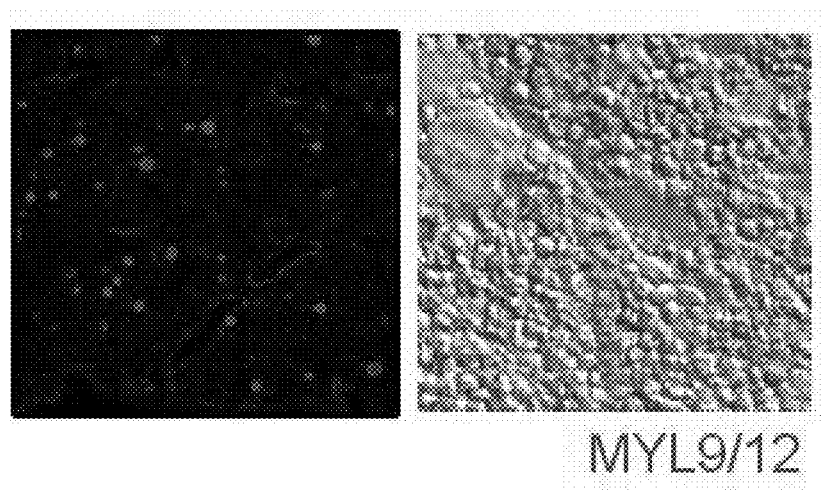
FIG. 3C is an image showing that Myl9, Myl12a, or Myl12b was found in megakaryocytes and sinusoidal endothelial cells in bone marrow. The left panel represents an immunofluorescence staining image using anti-Myl9/12 antibody and the right panel represents a superimposed image of the immunofluorescence staining image and a bright field image (Example 3).

As shown in FIG. 3C, it was found that megakaryocytes and sinusoidal endothelial cells expressed Myl9, Myl12a, or Myl12b.

Further, in the megakaryocytes and the sinusoidal endothelial cells, the expression levels of mRNA of Myl9, Myl12a, or Myl12b were measured. The expression levels of mRNA of B cells and whole cells were also measured as subjects for comparison. Specifically, bone marrow of femur in a mouse was treated with collagenase IV and then VE-Cadherin$^+$PECAM$^+$CD45$^-$TER119$^-$ cells, CD41$^+$CD61$^+$CD19$^-$Gr1$^-$TCRβ$^-$ cells, and B220$^+$ cells were isolated with a FACSAria™ cell sorter (BD Biosciences) using anti-vascular endothelial cadherin (VE-cadherin) antibody, anti-CD45 antibody, anti-platelet endothelial cell adhesion molecule (PECAM) antibody, anti-TER119 antibody, anti-CD41 antibody, anti-CD61 antibody, anti-CD19 antibody, anti-Gr1 antibody, anti-TCR β antibody, and anti-B220 antibody, and were used as sinusoidal endothelial cells, megakaryocytes, and B cells, respectively.

Each of the cells and the bone marrow cells (whole) was treated with TRIzol™ (Invitrogen Life Technologies) to prepare its total RNA. The cDNA synthesis therefrom was carried out by using oligo (dT) primers and Superscrip™ II RT (Invitrogen Life Technologies). The cDNA was analyzed by using a quantitative RT-PCR with Applied Biosystems™ 7500 Fast Real-Time PCR System. TaqMan probes for Myl9, Myl12a, and Myl12b, which were used for the analysis, were each purchased from Applied Biosystems. In addition, β-actin was detected by using probes and primers (β-Actin forward: CTAAGGCCAACCGTGAAAAG-3' (SEQ ID NO: 22) and β-Actin reverse: 5'-ACCAGAG-GCATACAGGGACA (SEQ ID NO: 23)) manufactured by Roche Applied Science.

Figure 3D:
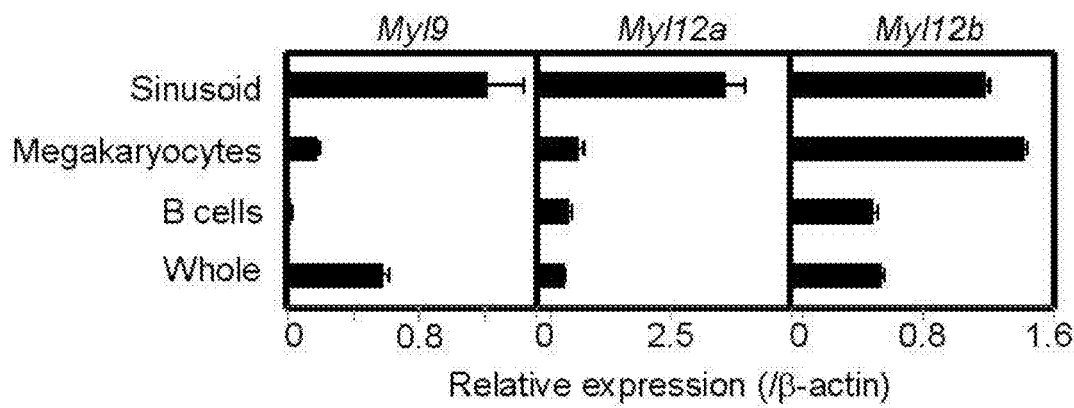
FIG. 3D is a graph for showing that high expression of each mRNA of Myl9, Myl12a, and Myl12b was found in sinusoidal endothelial cells isolated from bone marrow and high expression of Myl12b mRNA was found in megakaryocytes. Meanwhile, in B cells isolated from bone marrow and whole cells of bone marrow, expression levels of mRNAs of Myl9, Myl12a, and Myl12b were low. The horizontal axis represents relative expression of each mRNA of Myl9, Myl12a, and Myl12b to the expression level of β-actin (β-actin) (Relative expression) (Example 3).

As shown in FIG. 3D, it was proved that all the expression levels of Myl9, Myl12a, and Myl12b were high in the sinusoidal endothelial cells. In addition, it was found that the expression level of Myl12b was high in the megakaryocytes as well.

Further, expression levels of Myl9, Myl12a, and Myl12b on cell surfaces were examined with a flow cytometer. Specifically, mouse femur was stained using anti-VE-cadherin antibody and anti-Myl9/12 antibody. Living cells indicating PI$^-$ were detected with propidium iodide (PI, Sigma-Aldrich Co. LLC.), and expression levels of Myl9 and Myl12 in bone marrow cells (Whole) and VE-cadherin+ sinusoidal endothelial cells from the detected cells were analyzed with FACSCanto2 (BD Biosciences).

Figure 3E:
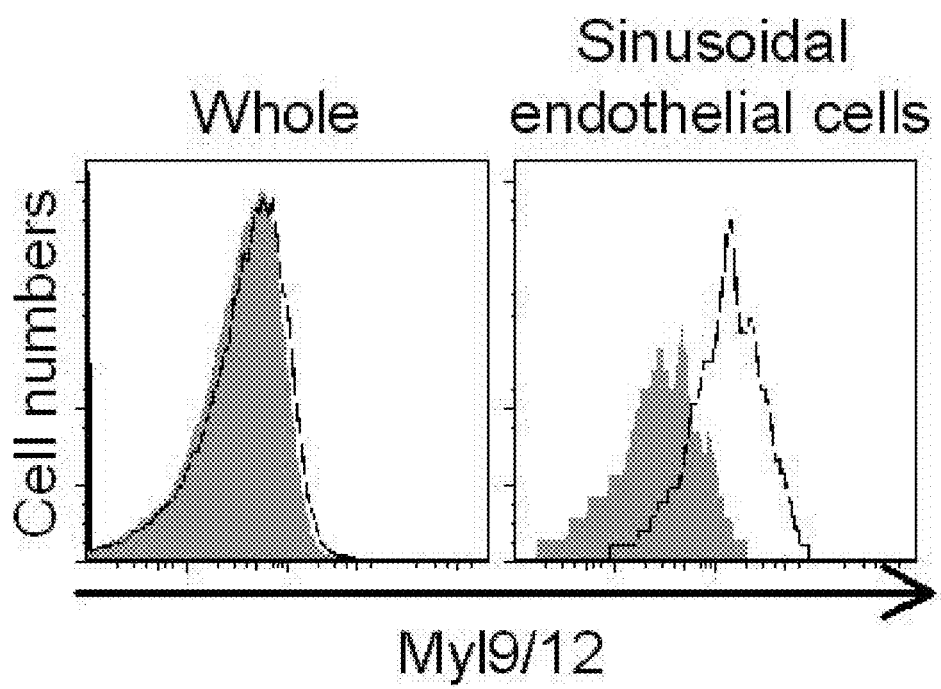
FIG. 3E is a graph for showing that analyses using a flow cytometer revealed that Myl9, Myl12a, and Myl12b were expressed on cell surfaces of sinusoidal endothelial cells in bone marrow. The vertical axis represents cell numbers and the horizontal axis represents staining intensities using anti-Myl9/12 antibody.

As shown in FIG. 3E, in the bone marrow cells, substantially no expression of Myl9, Myl12a, and Myl12b was found (left panel), while in the sinusoidal endothelial cells (VE-cadherin+ cells), the expression of Myl9, Myl12a, or Myl12b was found (right panel).

In addition, it was investigated whether Myl9 or Myl12 was expressed on a cell surface in a mouse body. Specifically, 10 μg of anti-Myl9/12 antibody labeled with Cy5 was administered to a mouse via tail vein and a bone marrow tissue section in the mouse 30 minutes after the administration was subjected to immunostaining using anti-VE-cadherin antibody and CellMask™ (Invitrogen).

Figure 3F:
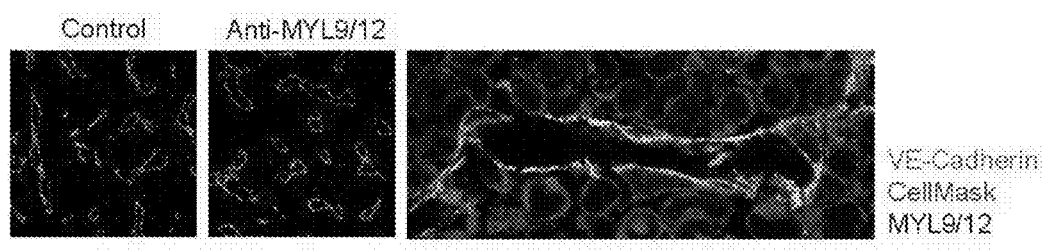
FIG. 3F is an image for showing that in a mouse body, sinusoidal endothelial cells (VE-cadherin$^+$ cells) expressed Myl9, Myl12a, or Myl12b, and the expression was found outside of a cell lipid bilayer membrane labeled by CellMask$^+$, that is, a cell surface. The analyses were performed for tissue sections of bone marrow in a mouse given 10 μg of anti-Myl9/12 antibody labeled with Cy5 through tail vein by inmmunostaining using anti-VE-cadherin antibody and CellMask™ (Invitrogen) (Example 3).

As shown in FIG. 3F, it was proved that the sinusoidal endothelial cells (VE-cadherin+ cells) expressed Myl9, Myl12a, or Myl12b and the expression was found outside of a cell lipid bilayer membrane labeled by CellMask+, that is, a cell surface.

Example 4

It has been reported that CD69 plays a key role in allergic airway inflammation (Non Patent Literature 6). Therefore, the investigation of the involvement of Myl9, Myl12a, and Myl12b, which have been proved to bind with CD69, in allergic airway inflammation and the investigation of the inhibition effect of administration of anti-Myl9/12 antibody on airway inflammation were performed.

Figure 4:
FIG. 4 is a view for illustrating a specific recognition site of the anti-Myl9/12 antibody used in FIG. 2D, FIG. 3A, FIG. 3C, FIG. 3E, FIG. 3F, FIG. 5A, and FIG. 5C in Myl9.

The anti-Myl9/12 antibody (MEDICAL & BIOLOGICAL LABORATORIES CO., LTD.) used in some of the Examples is a polyclonal antibody produced at MEDICAL & BIOLOGICAL LABORATORIES CO., LTD. by using, as an antigen, a peptide having keyhole limpet hemocyanin (KLH) bound to amino acid residues at positions 1 to 27 on the N-terminal side of Myl9, and immunizing the peptide to a rabbit. The amino acid sequence of the peptide is an amino acid sequence on the N-terminal side of EF-hand domain, is conserved in humans and mice, and is present on the N-terminal side of Myl12a and Myl12b as well. Thus, it is considered that the antibody of the present invention specifically recognizes a domain which includes amino acid sequences on the N-terminal side of Myl9, Myl12a, and Myl12b in humans and mice (FIG. 4).

Firstly, airway inflammation was induced in mice to examine the expression of Myl9, Myl12a, or Myl12b in the lung tissue sections. Specifically, on Day 0 and Day 7, 100 big/mouse of ovalbumin (OVA) (Sigma-Aldrich Co. LLC.) was intraperitoneally administered to a C57BL/6 mouse together with 4 mg/mouse of alum (Thermo Fisher Scientific K.K.) for immunization. Then, on Days 14, 15, and 16, the mouse was sensitized by inhalation of PBS or 1% OVA (Sigma-Aldrich Co. LLC.) to induce airway inflammation. An ultrasonic nebulizer was used for the inhalation of OVA (OMRON Corporation). A mouse which inhaled PBS (Control) was used as a control and a mouse which inhaled OVA (Inhalation) was used as an inflammation-induced sample. On Day 18, 48 hours after the exposure to inhalation, the mouse lung was fixed with 4% paraformaldehyde, followed by replacement with 30% sucrose. Rabbit anti-Myl9 antibody (Abcam plc.; recognizing Myl12a and Myl12b as well) was used as a primary antibody and Alexa 488-labeled anti-rabbit IgG antibody was used as a secondary antibody. TOPRO3 (Invitrogen) and Cell Mask (CellMask™ orange plasma membrane stain) (Invitrogen) were used for detection of nuclear staining (Nucleus) and lipid staining (staining the vicinity of cytoplasm (Cytosol) as well). A staining procedure was performed in accordance with the instruction and histological analysis was performed with a confocal laser microscope LSM710 (Carl Zeiss).

Figure 5A:
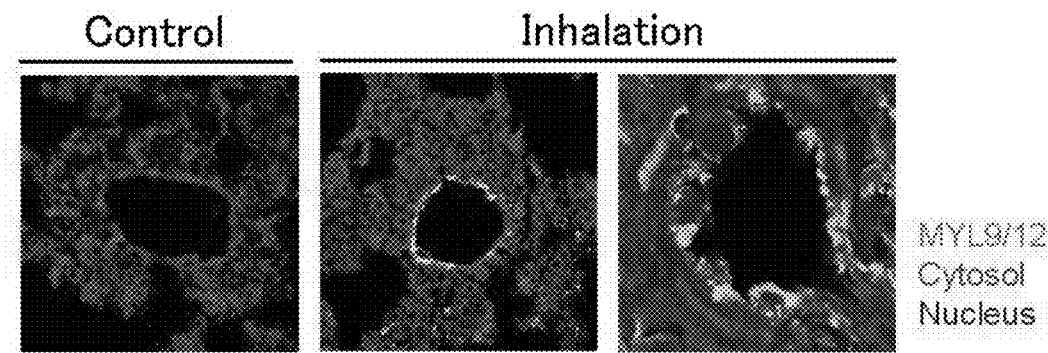
FIG. 5A is an image for showing that the expression of Myl9, Myl12a, or Myl12b was found on the surface of a vascular endothelial cell of a lung tissue section in the mouse in which airway inflammation was induced. Meanwhile, in the lung tissue section of the mouse in which airway inflammation was not induced, the expression was not found. The left panel indicates the results of the mouse in which airway inflammation was not induced. The center panel and the right panel indicate the results of the mouse in which airway inflammation was induced (Example 4).

As shown in FIG. 5A, in the lung tissue section of the inflammation-induced mouse, the expression of Myl9, Myl12a, or Myl12b was found on the vascular endothelial cell surface (center panel and right panel). Meanwhile, in the lung tissue section of the mouse in which airway inflammation was not induced, the expression was not found (left panel of FIG. 5A).

Then, the expression of Myl9, Myl12a, or Myl12b in the lung of the mouse in which airway inflammation was induced was investigated by immunoblotting. Specifically, the lung of a C57BL/6 mouse immunized and sensitized by the same method as described above was treated with collagenase IV (Sigma-Aldrich Co. LLC.) and then the lung was lysed with a protease inhibitor (Roche Diagnostics K.K.)-containing lysis buffer (20 mM Tris-HCl (pH 8.0), 150 mM NaCl, 0.05% NaN$_3$, 10% glycerol, 1% Triton-X100™). The obtained lung extract was separated by SDS-PAGE and then transferred to a PVDF membrane (Bio-Rad Laboratories, Inc.). Rabbit anti-Myl9 antibody (Abcamplc.) and mouse anti-α-tubulin antibody (NeoMarckers) were used as primary antibodies. Anti-rabbit IgG antibody (Cell Signaling Technology, Inc.) and anti-mouse IgG antibody (GE Healthcare) each labeled with HRP were used as secondary antibodies. Each of the proteins was detected with ChemiDocXRS+(Bio-Rad Laboratories, Inc.) using ECL-Detection Reagents (GE Healthcare).

Figure 5B:
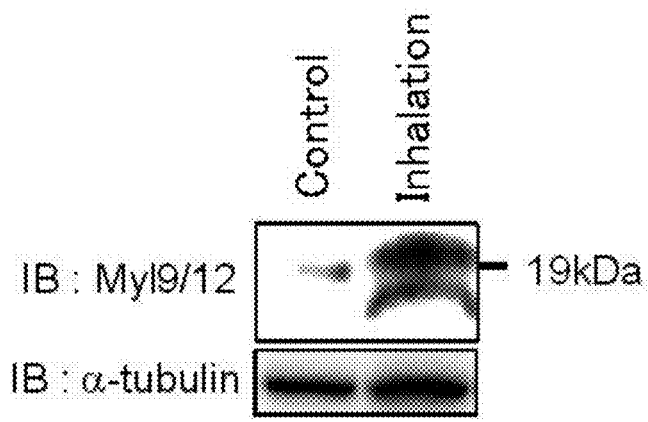
FIG. 5B is an image for showing that in an extract prepared from the lung of the mouse in which airway inflammation was induced, it was found that the expression of Myl9/12a/12b was increased compared to a non-inflammation-induced lung extract.

As shown in FIG. 5B, an increase in expression of Myl9/12a/12b was found in the inflammation-induced lung extract compared to the non-inflammation-induced lung extract.

From those results, it can be considered that Myl9, Myl12a, and Myl12b contribute to allergic airway inflammation in which CD69 was involved.

Therefore, it was investigated whether airway inflammation was inhibited by administration of anti-Myl9/12 antibody. Firstly, on Day 0 and Day 7, 100 μg/mouse of OVA (Sigma-Aldrich Co. LLC.) was intraperitoneally administered to a BALE/c mouse together with 4 mg/mouse of alum (Thermo Fisher Scientific K. K.) for immunization. On Days 14 and 16, the mouse was sensitized by inhalation of a 1% OVA solution (Sigma-Aldrich Co. LLC.). An ultrasonic nebulizer was used for the inhalation of OVA (OMRON Corporation). On Day 13 and Day 15, 1 day before the sensitization, rabbit anti-Myl9/12 antibody (MEDICAL & BIOLOGICAL LABORATORIES CO., LTD.) or Armenian hamster anti-CD69 antibody (eBioscience) was intraperitoneally administered to the mouse at 100 μg/mouse. Rabbit IgG (Jackson ImmunoResearch Labs, Inc.) was used as a control antibody and was intraperitoneally administered to the mouse at 100 μg/mouse in the same manner. On Day 17, alveolar lavage was performed, and infiltrating cells in bronchoalveolar lavage were compared among the anti-Myl9/12 antibody administration group, the anti-CD69 antibody administration group, and the control antibody administration group. The alveolar lavage was performed by intraperitoneally administering pentobarbital Na (70 mg/kg to 90 mg/kg) to the mouse for anesthetization, then incising the respiratory tract to insert a cannula (Becton, Dickinson and Company), and injecting physiological saline (Otsuka Pharmaceutical Co., Ltd.) into the lung to collect cells. The collected cells were suspended in fetal calf serum (FCS) and attached onto a glass slide using a cytospin 3 (Thermo Fisher Scientific K.K.). Giemsa staining was performed with May-Gruenwald Giemsa (Merck KGaA) reagent, 5×10² cells per glass slide were counted, and the cells were identified as eosinophils (Eo), neutrophils (Neu), lymphocytes (Lym), and macrophages (MΦ) according to morphological criteria.

Figure 5C:
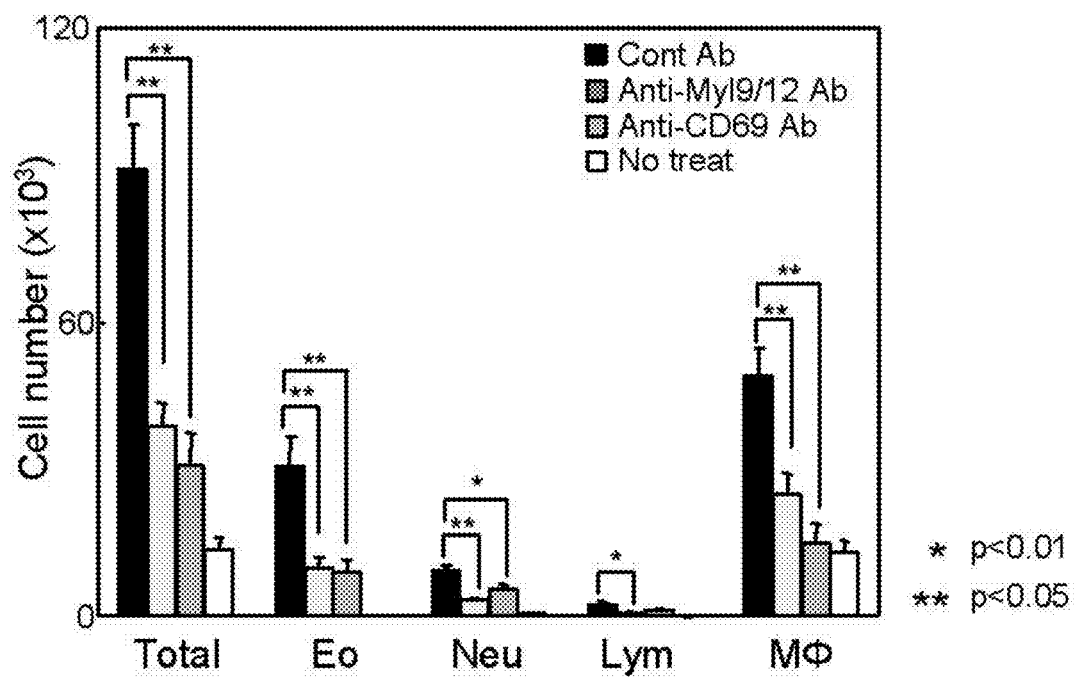
FIG. 5C is a graph for showing that in the mouse in which airway inflammation was induced, infiltration of eosinophils, neutrophils, lymphocytes, and macrophages in bronchoalveolar lavage was found, but the infiltration of these cells was significantly suppressed by administration of anti-Myl9/12 antibody before sensitization with an antigen. Suppression of infiltration of cells by the administration of anti-Myl9/12 antibody (Anti-Myl9/12Ab) was comparable to the suppression effect by administration of anti-CD69 antibody (Anti-CD69Ab). In addition, in a control antibody (Cont Ab), infiltration of cells was not suppressed. The vertical axis represents cell numbers (Cell number).

As shown in FIG. 5C, in the anti-Myl9/12 antibody administration group, the eosinophils, neutrophils, lymphocytes, and macrophages in the infiltrating cells were significantly decreased to the same extent as that of the anti-CD69 antibody administration group. In addition, on Day 17, an increase in methacholine-induced airway resistance was measured, and as a result, in the control antibody administration group, the airway resistance value was increased in a methacholine concentration-dependent manner, while in the anti-Myl9/12 antibody administration group, the airway resistance value was decreased with no significant difference (data not shown).

From those results, it was suggested that Myl9, Myl12a, and Myl12b were specifically expressed in inflammation-induced vascular endothelial cells and administration of anti-Myl9/12 antibody led to attenuation of airway inflammation.

INDUSTRIAL APPLICABILITY

The composition containing an anti-myosin regulatory light chain polypeptide antibody according to the present invention is useful for treatment of an inflammatory disease. In addition, the method of identifying a compound according to the present invention is useful for identification of a candidate compound that serves as an active ingredient of a composition for treating an inflammatory disease. Accordingly, the present invention is useful in the field of medicine including development of a pharmaceutical for an inflammatory disease and treatment of the inflammatory disease.

SEQUENCE LISTING FREE TEXT

SEQ ID NO: 1: (1):(519) coding region.
SEQ ID NO: 1: nucleotide sequence of DNA encoding human Myl9 isoform a.

SEQ ID NO: 3: (1):(357) coding region.
SEQ ID NO: 3: nucleotide sequence of DNA encoding human Myl9 isoform b.

SEQ ID NO: 5: (1):(516) coding region.
SEQ ID NO: 5: nucleotide sequence of DNA encoding human Myl12 isoform a.

SEQ ID NO: 7: (1):(519) coding region.
SEQ ID NO: 7: nucleotide sequence of transcript variant 1 encoding human Myl12 isoform b.

SEQ ID NO: 9: (1):(519) coding region.
SEQ ID NO: 9: nucleotide sequence of transcript variant 2 encoding human Myl12 isoform b.

SEQ ID NO: 11: (1):(519) coding region.
SEQ ID NO: 11: nucleotide sequence of transcript variant 3 encoding human Myl12 isoform b.

SEQ ID NO: 13: (1):(519) coding region.
SEQ ID NO: 13: nucleotide sequence of DNA encoding mouse Myl9.

SEQ ID NO: 15: (1):(519) coding region.
SEQ ID NO: 15: nucleotide sequence of DNA encoding mouse Myl12 isoform a.

SEQ ID NO: 17: (1):(519) coding region.
SEQ ID NO: 17: nucleotide sequence of DNA encoding mouse Myl12 isoform b.

SEQ ID NO: 19: (1):(600) coding region.
SEQ ID NO: 19: nucleotide sequence of DNA encoding human CD69.

SEQ ID NO: 21: tag peptide.

SEQ ID NO: 22: oligonucleotide designed for a primer.

SEQ ID NO: 23: oligonucleotide designed for a primer.

SEQ ID NO: 24: amino acid sequence having extremely high homology with amino acid sequences of N-terminal parts of Myl9, Myl12a, and Myl12b.

---

What is claimed is:

1. A method of identifying a compound that inhibits a result of an effect of coexistence of myosin regulatory light chain polypeptide (Myl) with CD69, comprising:

allowing Myl to coexist with CD69 in the presence of a test compound;

subsequently measuring an effect of coexistence of Myl with CD69; and determining that the test compound inhibits a result of an effect of coexistence of Myl with CD69 when reduction or disappearance of the effect is detected.

2. The method of identifying a compound according to claim 1, wherein the effect of coexistence of Myl with CD69 is a binding of Myl with CD69.

3. The method of identifying a compound according to claim 1, wherein the Myl is any one selected from the group consisting of Myl9, Myl12a, and Myl12b.

4. The method of claim 1, further comprising treating an inflammatory disease with said test compound, wherein said test compound is a polyclonal antibody that specifically recognizes Myl and inhibits binding of Myl with CD69.

5. A method of identifying a candidate compound that serves as an active ingredient of a composition for treating an inflammatory disease, comprising
selecting a compound that inhibits a result of an effect of coexistence of myosin regulatory light chain polypeptide (Myl) with CD69; and
treating an inflammatory disease with said compound, wherein said compound is a polyclonal antibody that specifically recognizes Myl and inhibits binding of Myl with CD69.

6. The method of identifying a candidate compound according to claim 5, wherein the effect of coexistence of Myl with CD69 is a binding of Myl with CD69.

7. The method of identifying a candidate compound according to claim 5, wherein the Myl is any one selected from the group consisting of Myl9, Myl12a, and Myl12b.

* * * * *

SEQUENCE LISTING

```
<160> NUMBER OF SEQ ID NOS: 24

<210> SEQ ID NO 1
<211> LENGTH: 519
<212> TYPE: DNA
<213> ORGANISM: homo sapiens
<220> FEATURE:
<221> NAME/KEY: misc_feature
<223> OTHER INFORMATION: nucleotide sequence of DNA encoding human myl9
      isoform a
<220> FEATURE:
<221> NAME/KEY: CDS
<222> LOCATION: (1)..(519)

<400> SEQUENCE: 1 atg tcc agc aag cgg gcc aaa gcc aag acc acc aag aag cgg cca cag      48
Met Ser Ser Lys Arg Ala Lys Ala Lys Thr Thr Lys Lys Arg Pro Gln
1               5                   10                  15 cgg gcc aca tcc aat gtc ttc gca atg ttt gac cag tcc cag atc cag      96
Arg Ala Thr Ser Asn Val Phe Ala Met Phe Asp Gln Ser Gln Ile Gln
            20                  25                  30 gag ttt aag gag gct ttc aac atg att gac cag aac cgt gat ggc ttc     144
Glu Phe Lys Glu Ala Phe Asn Met Ile Asp Gln Asn Arg Asp Gly Phe
```

```
                35                  40                  45
att gac aag gag gac ctg cac gac atg ctg gcc tcg ctg ggg aag aac        192
Ile Asp Lys Glu Asp Leu His Asp Met Leu Ala Ser Leu Gly Lys Asn
 50                  55                  60 ccc aca gac gaa tac ctg gag ggc atg atg agc gag gcc ccg ggg ccc        240
Pro Thr Asp Glu Tyr Leu Glu Gly Met Met Ser Glu Ala Pro Gly Pro
 65                  70                  75                  80 atc aac ttc acc atg ttc ctc acc atg ttt ggg gag aag ctg aac ggc        288
Ile Asn Phe Thr Met Phe Leu Thr Met Phe Gly Glu Lys Leu Asn Gly
                 85                  90                  95 acg gac ccc gag gat gtg att cgc aac gcc ttt gcc tgc ttc gac gag        336
Thr Asp Pro Glu Asp Val Ile Arg Asn Ala Phe Ala Cys Phe Asp Glu
            100                 105                 110 gaa gcc tca ggt ttc atc cat gag gac cac ctc cgg gag ctg ctc acc        384
Glu Ala Ser Gly Phe Ile His Glu Asp His Leu Arg Glu Leu Leu Thr
        115                 120                 125 acc atg ggt gac cgc ttc aca gat gag gaa gtg gac gag atg tac cgg        432
Thr Met Gly Asp Arg Phe Thr Asp Glu Glu Val Asp Glu Met Tyr Arg
    130                 135                 140 gag gca ccc att gat aag aaa ggc aac ttc aac tac gtg gag ttc acc        480
Glu Ala Pro Ile Asp Lys Lys Gly Asn Phe Asn Tyr Val Glu Phe Thr
145                 150                 155                 160 cgc atc ctc aaa cat ggc gcc aag gat aaa gac gac tag                    519
Arg Ile Leu Lys His Gly Ala Lys Asp Lys Asp Asp
                165                 170
```

<210> SEQ ID NO 2
<211> LENGTH: 172
<212> TYPE: PRT
<213> ORGANISM: homo sapiens

<400> SEQUENCE: 2

```
Met Ser Ser Lys Arg Ala Lys Ala Lys Thr Thr Lys Lys Arg Pro Gln
  1               5                  10                  15

Arg Ala Thr Ser Asn Val Phe Ala Met Phe Asp Gln Ser Gln Ile Gln
                 20                  25                  30

Glu Phe Lys Glu Ala Phe Asn Met Ile Asp Gln Asn Arg Asp Gly Phe
             35                  40                  45

Ile Asp Lys Glu Asp Leu His Asp Met Leu Ala Ser Leu Gly Lys Asn
 50                  55                  60

Pro Thr Asp Glu Tyr Leu Glu Gly Met Met Ser Glu Ala Pro Gly Pro
 65                  70                  75                  80

Ile Asn Phe Thr Met Phe Leu Thr Met Phe Gly Glu Lys Leu Asn Gly
                 85                  90                  95

Thr Asp Pro Glu Asp Val Ile Arg Asn Ala Phe Ala Cys Phe Asp Glu
            100                 105                 110

Glu Ala Ser Gly Phe Ile His Glu Asp His Leu Arg Glu Leu Leu Thr
        115                 120                 125

Thr Met Gly Asp Arg Phe Thr Asp Glu Glu Val Asp Glu Met Tyr Arg
    130                 135                 140

Glu Ala Pro Ile Asp Lys Lys Gly Asn Phe Asn Tyr Val Glu Phe Thr
145                 150                 155                 160

Arg Ile Leu Lys His Gly Ala Lys Asp Lys Asp Asp
                165                 170
```

<210> SEQ ID NO 3
<211> LENGTH: 357
<212> TYPE: DNA

<213> ORGANISM: homo sapiens
<220> FEATURE:
<221> NAME/KEY: misc_feature
<223> OTHER INFORMATION: nucleotide sequence of DNA encoding human myl9 isoform b
<220> FEATURE:
<221> NAME/KEY: CDS
<222> LOCATION: (1)..(357)

<400> SEQUENCE: 3

```
atg tcc agc aag cgg gcc aaa gcc aag acc acc aag aag cgg cca cag      48
Met Ser Ser Lys Arg Ala Lys Ala Lys Thr Thr Lys Lys Arg Pro Gln
1               5                   10                  15 cgg gcc aca tcc aat gtc ttc gca atg ttt gac cag tcc cag atc cag      96
Arg Ala Thr Ser Asn Val Phe Ala Met Phe Asp Gln Ser Gln Ile Gln
                20                  25                  30 gag ttt aag gag gct ttc aac atg att gac cag aac cgt gat ggc ttc     144
Glu Phe Lys Glu Ala Phe Asn Met Ile Asp Gln Asn Arg Asp Gly Phe
        35                  40                  45 att gac aag gag gac ctg cac gac atg ctg gcc tcg ctg ggt ttc atc     192
Ile Asp Lys Glu Asp Leu His Asp Met Leu Ala Ser Leu Gly Phe Ile
50                  55                  60 cat gag gac cac ctc cgg gag ctg ctc acc acc atg ggt gac cgc ttc     240
His Glu Asp His Leu Arg Glu Leu Leu Thr Thr Met Gly Asp Arg Phe
65                  70                  75                  80 aca gat gag gaa gtg gac gag atg tac cgg gag gca ccc att gat aag     288
Thr Asp Glu Glu Val Asp Glu Met Tyr Arg Glu Ala Pro Ile Asp Lys
                85                  90                  95 aaa ggc aac ttc aac tac gtg gag ttc acc cgc atc ctc aaa cat ggc     336
Lys Gly Asn Phe Asn Tyr Val Glu Phe Thr Arg Ile Leu Lys His Gly
            100                 105                 110 gcc aag gat aaa gac gac tag                                         357
Ala Lys Asp Lys Asp Asp
            115
```

<210> SEQ ID NO 4
<211> LENGTH: 118
<212> TYPE: PRT
<213> ORGANISM: homo sapiens

<400> SEQUENCE: 4

```
Met Ser Ser Lys Arg Ala Lys Ala Lys Thr Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Leu Gly Phe Ile
50                  55                  60

His Glu Asp His Leu Arg Glu Leu Leu Thr Thr Met Gly Asp Arg Phe
65                  70                  75                  80

Thr Asp Glu Glu Val Asp Glu Met Tyr Arg Glu Ala Pro Ile Asp Lys
                85                  90                  95

Lys Gly Asn Phe Asn Tyr Val Glu Phe Thr Arg Ile Leu Lys His Gly
            100                 105                 110

Ala Lys Asp Lys Asp Asp
            115
```

<210> SEQ ID NO 5
<211> LENGTH: 516
<212> TYPE: DNA

<213> ORGANISM: homo sapiens
<220> FEATURE:
<221> NAME/KEY: misc_feature
<223> OTHER INFORMATION: nucleotide sequence of DNA encoding human myl12 isoform a
<220> FEATURE:
<221> NAME/KEY: CDS
<222> LOCATION: (1)..(516)

<400> SEQUENCE: 5

```
atg tcg agc aaa aga aca aag acc aag acc aag aag cgc cct cag cgt    48
Met Ser Ser Lys Arg Thr Lys Thr Lys Thr Lys Lys Arg Pro Gln Arg
1               5                   10                  15 gca aca tcc aat gtg ttt gct atg ttt gac cag tcg cag att cag gag    96
Ala Thr Ser Asn Val Phe Ala Met Phe Asp Gln Ser Gln Ile Gln Glu
            20                  25                  30 ttc aaa gag gcc ttc aac atg att gat cag aac aga gat ggt ttc atc   144
Phe Lys Glu Ala Phe Asn Met Ile Asp Gln Asn Arg Asp Gly Phe Ile
        35                  40                  45 gac aag gaa gat ttg cat gat atg ctt gct tca ttg ggg aag aat cca   192
Asp Lys Glu Asp Leu His Asp Met Leu Ala Ser Leu Gly Lys Asn Pro
    50                  55                  60 act gat gag tat cta gat gcc atg atg aat gag gct cca ggc ccc atc   240
Thr Asp Glu Tyr Leu Asp Ala Met Met Asn Glu Ala Pro Gly Pro Ile
65                  70                  75                  80 aat ttc acc atg ttc ctc acc atg ttt ggt gag aag tta aat ggc aca   288
Asn Phe Thr Met Phe Leu Thr Met Phe Gly Glu Lys Leu Asn Gly Thr
                85                  90                  95 gat cct gaa gat gtc atc aga aat gcc ttt gct tgc ttt gat gaa gaa   336
Asp Pro Glu Asp Val Ile Arg Asn Ala Phe Ala Cys Phe Asp Glu Glu
            100                 105                 110 gca act ggc acc ata cag gaa gat tac ttg aga gag ctg ctg aca acc   384
Ala Thr Gly Thr Ile Gln Glu Asp Tyr Leu Arg Glu Leu Leu Thr Thr
        115                 120                 125 atg ggg gat cgg ttt aca gat gag gaa gtg gat gag ctg tac aga gaa   432
Met Gly Asp Arg Phe Thr Asp Glu Glu Val Asp Glu Leu Tyr Arg Glu
    130                 135                 140 gca cct att gat aaa aag ggg aat ttc aat tac atc gag ttc aca cgc   480
Ala Pro Ile Asp Lys Lys Gly Asn Phe Asn Tyr Ile Glu Phe Thr Arg
145                 150                 155                 160 atc ctg aaa cat gga gcc aaa gac aaa gat gac tga                   516
Ile Leu Lys His Gly Ala Lys Asp Lys Asp Asp
                165                 170
```

<210> SEQ ID NO 6
<211> LENGTH: 171
<212> TYPE: PRT
<213> ORGANISM: homo sapiens

<400> SEQUENCE: 6

```
Met Ser Ser Lys Arg Thr Lys Thr Lys Thr Lys Lys Arg Pro Gln Arg
1               5                   10                  15

Ala Thr Ser Asn Val Phe Ala Met Phe Asp Gln Ser Gln Ile Gln Glu
            20                  25                  30

Phe Lys Glu Ala Phe Asn Met Ile Asp Gln Asn Arg Asp Gly Phe Ile
        35                  40                  45

Asp Lys Glu Asp Leu His Asp Met Leu Ala Ser Leu Gly Lys Asn Pro
    50                  55                  60

Thr Asp Glu Tyr Leu Asp Ala Met Met Asn Glu Ala Pro Gly Pro Ile
65                  70                  75                  80

Asn Phe Thr Met Phe Leu Thr Met Phe Gly Glu Lys Leu Asn Gly Thr
```

```
                85                  90                  95
Asp Pro Glu Asp Val Ile Arg Asn Ala Phe Ala Cys Phe Asp Glu Glu
            100                 105                 110

Ala Thr Gly Thr Ile Gln Glu Asp Tyr Leu Arg Glu Leu Leu Thr Thr
            115                 120                 125

Met Gly Asp Arg Phe Thr Asp Glu Glu Val Asp Glu Leu Tyr Arg Glu
            130                 135                 140

Ala Pro Ile Asp Lys Lys Gly Asn Phe Asn Tyr Ile Glu Phe Thr Arg
145                 150                 155                 160

Ile Leu Lys His Gly Ala Lys Asp Lys Asp Asp
                165                 170

<210> SEQ ID NO 7
<211> LENGTH: 519
<212> TYPE: DNA
<213> ORGANISM: homo sapiens
<220> FEATURE:
<221> NAME/KEY: misc_feature
<223> OTHER INFORMATION: nucleotide sequence of transcript variant 1
      encoding human myl12 isoform b
<220> FEATURE:
<221> NAME/KEY: CDS
<222> LOCATION: (1)..(519)

<400> SEQUENCE: 7 atg tcg agc aaa aag gca aag acc aag acc acc aag aag cgc cct cag      48
Met Ser Ser Lys Lys Ala Lys Thr Lys Thr Thr Lys Lys Arg Pro Gln
1               5                   10                  15 cgt gca aca tcc aat gtg ttt gcc atg ttt gac cag tca cag att cag      96
Arg Ala Thr Ser Asn Val Phe Ala Met Phe Asp Gln Ser Gln Ile Gln
                20                  25                  30 gag ttc aaa gag gcc ttc aac atg att gat cag aac aga gat ggc ttc     144
Glu Phe Lys Glu Ala Phe Asn Met Ile Asp Gln Asn Arg Asp Gly Phe
            35                  40                  45 atc gac aag gaa gat ttg cat gat atg ctt gct tct cta ggg aag aat     192
Ile Asp Lys Glu Asp Leu His Asp Met Leu Ala Ser Leu Gly Lys Asn
        50                  55                  60 ccc act gat gca tac ctt gat gcc atg atg aat gag gcc cca ggg ccc     240
Pro Thr Asp Ala Tyr Leu Asp Ala Met Met Asn Glu Ala Pro Gly Pro
65                  70                  75                  80 atc aat ttc acc atg ttc ctg acc atg ttt ggt gag aag tta aat ggc     288
Ile Asn Phe Thr Met Phe Leu Thr Met Phe Gly Glu Lys Leu Asn Gly
                85                  90                  95 aca gat cct gaa gat gtc atc aga aac gcc ttt gct tgc ttt gat gaa     336
Thr Asp Pro Glu Asp Val Ile Arg Asn Ala Phe Ala Cys Phe Asp Glu
            100                 105                 110 gaa gca aca ggc acc att cag gaa gat tac cta aga gag ctg ctg aca     384
Glu Ala Thr Gly Thr Ile Gln Glu Asp Tyr Leu Arg Glu Leu Leu Thr
        115                 120                 125 acc atg ggg gat cgg ttt aca gat gag gaa gtg gat gag ctg tac aga     432
Thr Met Gly Asp Arg Phe Thr Asp Glu Glu Val Asp Glu Leu Tyr Arg
130                 135                 140 gaa gca cct att gac aaa aag ggg aat ttc aat tac atc gag ttc aca     480
Glu Ala Pro Ile Asp Lys Lys Gly Asn Phe Asn Tyr Ile Glu Phe Thr
145                 150                 155                 160 cgc atc ctg aaa cat gga gcc aaa gac aaa gat gac tga                 519
Arg Ile Leu Lys His Gly Ala Lys Asp Lys Asp Asp
                165                 170

<210> SEQ ID NO 8
<211> LENGTH: 172
```

```
<212> TYPE: PRT
<213> ORGANISM: homo sapiens

<400> SEQUENCE: 8

Met Ser Ser Lys Lys Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
            35                  40                  45

Ile Asp Lys Glu Asp Leu His Asp Met Leu Ala Ser Leu Gly Lys Asn
        50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170

<210> SEQ ID NO 9
<211> LENGTH: 519
<212> TYPE: DNA
<213> ORGANISM: homo sapiens
<220> FEATURE:
<221> NAME/KEY: misc_feature
<223> OTHER INFORMATION: nucleotide sequence of transcript variant 2
      encoding human myl12 isoform b
<220> FEATURE:
<221> NAME/KEY: CDS
<222> LOCATION: (1)..(519)

<400> SEQUENCE: 9 atg tcg agc aaa aag gca aag acc aag acc acc aag aag cgc cct cag      48
Met Ser Ser Lys Lys Ala Lys Thr Lys Thr Thr Lys Lys Arg Pro Gln
1               5                   10                  15 cgt gca aca tcc aat gtg ttt gcc atg ttt gac cag tca cag att cag      96
Arg Ala Thr Ser Asn Val Phe Ala Met Phe Asp Gln Ser Gln Ile Gln
                20                  25                  30 gag ttc aaa gag gcc ttc aac atg att gat cag aac aga gat ggc ttc     144
Glu Phe Lys Glu Ala Phe Asn Met Ile Asp Gln Asn Arg Asp Gly Phe
            35                  40                  45 atc gac aag gaa gat ttg cat gat atg ctt gct tct cta ggg aag aat     192
Ile Asp Lys Glu Asp Leu His Asp Met Leu Ala Ser Leu Gly Lys Asn
        50                  55                  60 ccc act gat gca tac ctt gat gcc atg atg aat gag gcc cca ggg ccc     240
Pro Thr Asp Ala Tyr Leu Asp Ala Met Met Asn Glu Ala Pro Gly Pro
65                  70                  75                  80 atc aat ttc acc atg ttc ctg acc atg ttt ggt gag aag tta aat ggc     288
Ile Asn Phe Thr Met Phe Leu Thr Met Phe Gly Glu Lys Leu Asn Gly
                85                  90                  95 aca gat cct gaa gat gtc atc aga aac gcc ttt gct tgc ttt gat gaa     336
Thr Asp Pro Glu Asp Val Ile Arg Asn Ala Phe Ala Cys Phe Asp Glu
```

```
gaa gca aca ggc acc att cag gaa gat tac cta aga gag ctg ctg aca    384
Glu Ala Thr Gly Thr Ile Gln Glu Asp Tyr Leu Arg Glu Leu Leu Thr
            115                 120                 125 acc atg ggg gat cgg ttt aca gat gag gaa gtg gat gag ctg tac aga    432
Thr Met Gly Asp Arg Phe Thr Asp Glu Glu Val Asp Glu Leu Tyr Arg
        130                 135                 140 gaa gca cct att gac aaa aag ggg aat ttc aat tac atc gag ttc aca    480
Glu Ala Pro Ile Asp Lys Lys Gly Asn Phe Asn Tyr Ile Glu Phe Thr
145                 150                 155                 160 cgc atc ctg aaa cat gga gcc aaa gac aaa gat gac tga                519
Arg Ile Leu Lys His Gly Ala Lys Asp Lys Asp Asp
                165                 170

<210> SEQ ID NO 10
<211> LENGTH: 172
<212> TYPE: PRT
<213> ORGANISM: homo sapiens

<400> SEQUENCE: 10

Met Ser Ser Lys Lys Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Leu Gly Lys Asn
    50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
    130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170

<210> SEQ ID NO 11
<211> LENGTH: 519
<212> TYPE: DNA
<213> ORGANISM: homo sapiens
<220> FEATURE:
<221> NAME/KEY: misc_feature
<223> OTHER INFORMATION: nucleotide sequence of transcript variant 3
      encoding human myl12 isoform b
<220> FEATURE:
<221> NAME/KEY: CDS
<222> LOCATION: (1)..(519)

<400> SEQUENCE: 11 atg tcg agc aaa aag gca aag acc aag acc acc aag aag cgc cct cag     48
Met Ser Ser Lys Lys Ala Lys Thr Lys Thr Thr Lys Lys Arg Pro Gln
1               5                   10                  15 cgt gca aca tcc aat gtg ttt gcc atg ttt gac cag tca cag att cag     96
```

```
Arg Ala Thr Ser Asn Val Phe Ala Met Phe Asp Gln Ser Gln Ile Gln
             20                  25                  30 gag ttc aaa gag gcc ttc aac atg att gat cag aac aga gat ggc ttc       144
Glu Phe Lys Glu Ala Phe Asn Met Ile Asp Gln Asn Arg Asp Gly Phe
             35                  40                  45 atc gac aag gaa gat ttg cat gat atg ctt gct tct cta ggg aag aat       192
Ile Asp Lys Glu Asp Leu His Asp Met Leu Ala Ser Leu Gly Lys Asn
 50                  55                  60 ccc act gat gca tac ctt gat gcc atg atg aat gag gcc cca ggg ccc       240
Pro Thr Asp Ala Tyr Leu Asp Ala Met Met Asn Glu Ala Pro Gly Pro
 65                  70                  75                  80 atc aat ttc acc atg ttc ctg acc atg ttt ggt gag aag tta aat ggc       288
Ile Asn Phe Thr Met Phe Leu Thr Met Phe Gly Glu Lys Leu Asn Gly
                 85                  90                  95 aca gat cct gaa gat gtc atc aga aac gcc ttt gct tgc ttt gat gaa       336
Thr Asp Pro Glu Asp Val Ile Arg Asn Ala Phe Ala Cys Phe Asp Glu
            100                 105                 110 gaa gca aca ggc acc att cag gaa gat tac cta aga gag ctg ctg aca       384
Glu Ala Thr Gly Thr Ile Gln Glu Asp Tyr Leu Arg Glu Leu Leu Thr
            115                 120                 125 acc atg ggg gat cgg ttt aca gat gag gaa gtg gat gag ctg tac aga       432
Thr Met Gly Asp Arg Phe Thr Asp Glu Glu Val Asp Glu Leu Tyr Arg
        130                 135                 140 gaa gca cct att gac aaa aag ggg aat ttc aat tac atc gag ttc aca       480
Glu Ala Pro Ile Asp Lys Lys Gly Asn Phe Asn Tyr Ile Glu Phe Thr
145                 150                 155                 160 cgc atc ctg aaa cat gga gcc aaa gac aaa gat gac tga                   519
Arg Ile Leu Lys His Gly Ala Lys Asp Lys Asp Asp
                165                 170

<210> SEQ ID NO 12
<211> LENGTH: 172
<212> TYPE: PRT
<213> ORGANISM: homo sapiens

<400> SEQUENCE: 12

Met Ser Ser Lys Lys Ala Lys Thr Lys Thr Thr Lys Lys Arg Pro Gln
 1                5                  10                 15

Arg Ala Thr Ser Asn Val Phe Ala Met Phe Asp Gln Ser Gln Ile Gln
             20                  25                  30

Glu Phe Lys Glu Ala Phe Asn Met Ile Asp Gln Asn Arg Asp Gly Phe
             35                  40                  45

Ile Asp Lys Glu Asp Leu His Asp Met Leu Ala Ser Leu Gly Lys Asn
 50                  55                  60

Pro Thr Asp Ala Tyr Leu Asp Ala Met Met Asn Glu Ala Pro Gly Pro
 65                  70                  75                  80

Ile Asn Phe Thr Met Phe Leu Thr Met Phe Gly Glu Lys Leu Asn Gly
                 85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
            115                 120                 125

Thr Met Gly Asp Arg Phe Thr Asp Glu Glu Val Asp Glu Leu Tyr Arg
        130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170
```

<210> SEQ ID NO 13
<211> LENGTH: 519
<212> TYPE: DNA
<213> ORGANISM: mus musculus
<220> FEATURE:
<221> NAME/KEY: misc_feature
<223> OTHER INFORMATION: nucleotide sequence of DNA encoding mouse myl9
<220> FEATURE:
<221> NAME/KEY: CDS
<222> LOCATION: (1)..(519)

<400> SEQUENCE: 13

```
atg tcg agc aag aga gcc aag gcc aag acc acc aag aag agg ccc cag      48
Met Ser Ser Lys Arg Ala Lys Ala Lys Thr Thr Lys Lys Arg Pro Gln
1               5                   10                  15 agg gct acg tcc aat gtc ttc gcc atg ttt gac cag tcc cag atc cag      96
Arg Ala Thr Ser Asn Val Phe Ala Met Phe Asp Gln Ser Gln Ile Gln
                20                  25                  30 gag ttt aag gag gcc ttc aac atg att gat cag aac cga gat ggc ttc     144
Glu Phe Lys Glu Ala Phe Asn Met Ile Asp Gln Asn Arg Asp Gly Phe
            35                  40                  45 att gat aag gag gac ctg cac gac atg ctg gcc tct ctg ggg aag aac     192
Ile Asp Lys Glu Asp Leu His Asp Met Leu Ala Ser Leu Gly Lys Asn
    50                  55                  60 ccc aca gac gag tat ctg gag ggc atg atg aac gag gcg cca ggg ccc     240
Pro Thr Asp Glu Tyr Leu Glu Gly Met Met Asn Glu Ala Pro Gly Pro
65                  70                  75                  80 atc aac ttc acc atg ttc ctc aca atg ttt ggg gag aag ctg aac ggc     288
Ile Asn Phe Thr Met Phe Leu Thr Met Phe Gly Glu Lys Leu Asn Gly
                85                  90                  95 aca gac ccc gag gat gtg atc cgc aat gcc ttt gcc tgc ttt gat gag     336
Thr Asp Pro Glu Asp Val Ile Arg Asn Ala Phe Ala Cys Phe Asp Glu
                100                 105                 110 gag gcc tca ggc ttc atc cac gag gac cac ctg agg gag ctc ctc acc     384
Glu Ala Ser Gly Phe Ile His Glu Asp His Leu Arg Glu Leu Leu Thr
            115                 120                 125 acc atg ggc gac cga ttc acg gat gag gag gtg gac gag atg tac cgc     432
Thr Met Gly Asp Arg Phe Thr Asp Glu Glu Val Asp Glu Met Tyr Arg
    130                 135                 140 gag gca ccc att gat aag aag ggc aac ttc aac tac gtg gag ttc act     480
Glu Ala Pro Ile Asp Lys Lys Gly Asn Phe Asn Tyr Val Glu Phe Thr
145                 150                 155                 160 cgc atc ctc aaa cac ggc gcc aag gac aag gac gac taa                 519
Arg Ile Leu Lys His Gly Ala Lys Asp Lys Asp Asp
                165                 170
```

<210> SEQ ID NO 14
<211> LENGTH: 172
<212> TYPE: PRT
<213> ORGANISM: mus musculus

<400> SEQUENCE: 14

```
Met Ser Ser Lys Arg Ala Lys Ala Lys Thr Thr Lys Lys Arg Pro Gln
1               5                   10                  15

Arg Ala Thr Ser Asn Val Phe Ala Met Phe Asp Gln Ser Gln Ile Gln
                20                  25                  30

Glu Phe Lys Glu Ala Phe Asn Met Ile Asp Gln Asn Arg Asp Gly Phe
            35                  40                  45

Ile Asp Lys Glu Asp Leu His Asp Met Leu Ala Ser Leu Gly Lys Asn
    50                  55                  60
```

```
Pro Thr Asp Glu Tyr Leu Glu Gly Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Ser Gly Phe Ile His Glu Asp His Leu Arg Glu Leu Leu Thr
            115                 120                 125

Thr Met Gly Asp Arg Phe Thr Asp Glu Glu Val Asp Glu Met Tyr Arg
        130                 135                 140

Glu Ala Pro Ile Asp Lys Lys Gly Asn Phe Asn Tyr Val Glu Phe Thr
145                 150                 155                 160

Arg Ile Leu Lys His Gly Ala Lys Asp Lys Asp Asp
                165                 170
```

<210> SEQ ID NO 15
<211> LENGTH: 519
<212> TYPE: DNA
<213> ORGANISM: mus musculus
<220> FEATURE:
<221> NAME/KEY: misc_feature
<223> OTHER INFORMATION: nucleotide sequence of DNA encoding mouse myl12 isoform a
<220> FEATURE:
<221> NAME/KEY: CDS
<222> LOCATION: (1)..(519)

<400> SEQUENCE: 15

```
atg tct agc aaa agg gca aag acc aag acc acc aag aag cgc cct cag     48
Met Ser Ser Lys Arg Ala Lys Thr Lys Thr Thr Lys Lys Arg Pro Gln
1               5                   10                  15 cgc gca acc tcc aat gtg ttc gcc atg ttt gac cag tcc cag atc cag     96
Arg Ala Thr Ser Asn Val Phe Ala Met Phe Asp Gln Ser Gln Ile Gln
                20                  25                  30 gag ttc aaa gaa gcc ttt aac atg att gac cag aac cgg gat ggc ttc    144
Glu Phe Lys Glu Ala Phe Asn Met Ile Asp Gln Asn Arg Asp Gly Phe
        35                  40                  45 att gac aag gag gac ctg cac gac atg ctg gcg tca atg gga aaa aac    192
Ile Asp Lys Glu Asp Leu His Asp Met Leu Ala Ser Met Gly Lys Asn
50                  55                  60 cca act gac gaa tac ctg gac gcc atg atg aac gag gcc ccg ggc ccc    240
Pro Thr Asp Glu Tyr Leu Asp Ala Met Met Asn Glu Ala Pro Gly Pro
65                  70                  75                  80 atc aat ttc acc atg ttc ctc acc atg ttt ggg gag aag ctg aac ggc    288
Ile Asn Phe Thr Met Phe Leu Thr Met Phe Gly Glu Lys Leu Asn Gly
                85                  90                  95 act gac ccc gag gac gtc atc aga aac gcc ttc gct tgc ttt gat gag    336
Thr Asp Pro Glu Asp Val Ile Arg Asn Ala Phe Ala Cys Phe Asp Glu
            100                 105                 110 gaa gcc atc ggc acc atc cag gag gat tac ctg agg gag ctg ctg acc    384
Glu Ala Ile Gly Thr Ile Gln Glu Asp Tyr Leu Arg Glu Leu Leu Thr
            115                 120                 125 acc atg ggc gac cgc ttc aca gac gag gag gtg gat gag ctg tac aga    432
Thr Met Gly Asp Arg Phe Thr Asp Glu Glu Val Asp Glu Leu Tyr Arg
        130                 135                 140 gag gcc ccc att gac aaa aag ggg aac ttc aac tac att gag ttc aca    480
Glu Ala Pro Ile Asp Lys Lys Gly Asn Phe Asn Tyr Ile Glu Phe Thr
145                 150                 155                 160 cgc atc ctg aag cac ggc gcg aaa gac aaa gat gac tga                 519
Arg Ile Leu Lys His Gly Ala Lys Asp Lys Asp Asp
                165                 170
```

<210> SEQ ID NO 16
<211> LENGTH: 172
<212> TYPE: PRT
<213> ORGANISM: mus musculus

<400> SEQUENCE: 16

Met Ser Ser Lys Arg Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Met Gly Lys Asn
    50                  55                  60

Pro Thr Asp Glu Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Ile Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
    130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170

<210> SEQ ID NO 17
<211> LENGTH: 519
<212> TYPE: DNA
<213> ORGANISM: mus musculus
<220> FEATURE:
<221> NAME/KEY: misc_feature
<223> OTHER INFORMATION: nucleotide sequence of DNA encoding mouse myl12
     isoform b
<220> FEATURE:
<221> NAME/KEY: CDS
<222> LOCATION: (1)..(519)

<400> SEQUENCE: 17 atg tcg agc aaa aaa gcg aag acc aag acc acc aag aag cgc cct cag        48
Met Ser Ser Lys Lys Ala Lys Thr Lys Thr Thr Lys Lys Arg Pro Gln
1               5                   10                  15 cgc gca acc tcc aat gtg ttc gcc atg ttt gac cag tcc cag atc cag        96
Arg Ala Thr Ser Asn Val Phe Ala Met Phe Asp Gln Ser Gln Ile Gln
            20                  25                  30 gag ttc aaa gag gcc ttt aac atg att gac cag aac cgg gat ggc ttc       144
Glu Phe Lys Glu Ala Phe Asn Met Ile Asp Gln Asn Arg Asp Gly Phe
        35                  40                  45 att gac aag gag gac ctg cac gac atg ctg gcg tct ctg ggg aag aat       192
Ile Asp Lys Glu Asp Leu His Asp Met Leu Ala Ser Leu Gly Lys Asn
    50                  55                  60 ccc act gat gcc tac ctg gac gcc atg atg aac gag gcc ccg ggc ccc       240
Pro Thr Asp Ala Tyr Leu Asp Ala Met Met Asn Glu Ala Pro Gly Pro
65                  70                  75                  80 atc aat ttc acc atg ttc ctc acc atg ttt ggg gag aag cta aac ggc       288
Ile Asn Phe Thr Met Phe Leu Thr Met Phe Gly Glu Lys Leu Asn Gly

```
                85                   90                   95
act gac ccc gag gac gtc atc aga aac gcc ttc gct tgc ttt gat gag      336
Thr Asp Pro Glu Asp Val Ile Arg Asn Ala Phe Ala Cys Phe Asp Glu
            100                 105                 110 gaa gcc aca ggc acc atc cag gag gat tac ctg agg gag ctg ctg acc      384
Glu Ala Thr Gly Thr Ile Gln Glu Asp Tyr Leu Arg Glu Leu Leu Thr
        115                 120                 125 acc atg ggc gac cgc ttc aca gac gag gaa gtg gat gag ctg tac aga      432
Thr Met Gly Asp Arg Phe Thr Asp Glu Glu Val Asp Glu Leu Tyr Arg
    130                 135                 140 gag gcc ccc att gac aaa aag ggg aac ttc aac tac att gag ttc aca      480
Glu Ala Pro Ile Asp Lys Lys Gly Asn Phe Asn Tyr Ile Glu Phe Thr
145                 150                 155                 160 cgc atc ctg aag cac ggc gcg aaa gac aaa gat gac tga                  519
Arg Ile Leu Lys His Gly Ala Lys Asp Lys Asp Asp
                165                 170

<210> SEQ ID NO 18
<211> LENGTH: 172
<212> TYPE: PRT
<213> ORGANISM: mus musculus

<400> SEQUENCE: 18

Met Ser Ser Lys Lys Ala Lys Thr Lys Thr Thr Lys Lys Arg Pro Gln
1               5                   10                  15

Arg Ala Thr Ser Asn Val Phe Ala Met Phe Asp Gln Ser Gln Ile Gln
            20                  25                  30

Glu Phe Lys Glu Ala Phe Asn Met Ile Asp Gln Asn Arg Asp Gly Phe
        35                  40                  45

Ile Asp Lys Glu Asp Leu His Asp Met Leu Ala Ser Leu Gly Lys Asn
    50                  55                  60

Pro Thr Asp Ala Tyr Leu Asp Ala Met Met Asn Glu Ala Pro Gly Pro
65                  70                  75                  80

Ile Asn Phe Thr Met Phe Leu Thr Met Phe Gly Glu Lys Leu Asn Gly
                85                  90                  95

Thr Asp Pro Glu Asp Val Ile Arg Asn Ala Phe Ala Cys Phe Asp Glu
            100                 105                 110

Glu Ala Thr Gly Thr Ile Gln Glu Asp Tyr Leu Arg Glu Leu Leu Thr
        115                 120                 125

Thr Met Gly Asp Arg Phe Thr Asp Glu Glu Val Asp Glu Leu Tyr Arg
    130                 135                 140

Glu Ala Pro Ile Asp Lys Lys Gly Asn Phe Asn Tyr Ile Glu Phe Thr
145                 150                 155                 160

Arg Ile Leu Lys His Gly Ala Lys Asp Lys Asp Asp
                165                 170

<210> SEQ ID NO 19
<211> LENGTH: 600
<212> TYPE: DNA
<213> ORGANISM: homo sapiens
<220> FEATURE:
<221> NAME/KEY: misc_feature
<223> OTHER INFORMATION: nucleotide sequence of DNA encoding human CD69
<220> FEATURE:
<221> NAME/KEY: CDS
<222> LOCATION: (1)..(600)

<400> SEQUENCE: 19 atg agc tct gaa aat tgt ttc gta gca gag aac agc tct ttg cat ccg      48
Met Ser Ser Glu Asn Cys Phe Val Ala Glu Asn Ser Ser Leu His Pro
```

```
1               5                   10                  15
gag agt gga caa gaa aat gat gcc acc agt ccc cat ttc tca aca cgt      96
Glu Ser Gly Gln Glu Asn Asp Ala Thr Ser Pro His Phe Ser Thr Arg
            20                  25                  30 cat gaa ggg tcc ttc caa gtt cct gtc ctg tgt gct gta atg aat gtg     144
His Glu Gly Ser Phe Gln Val Pro Val Leu Cys Ala Val Met Asn Val
        35                  40                  45 gtc ttc atc acc att tta atc ata gct ctc att gcc tta tca gtg ggc     192
Val Phe Ile Thr Ile Leu Ile Ile Ala Leu Ile Ala Leu Ser Val Gly
    50                  55                  60 caa tac aat tgt cca ggc caa tac aca ttc tca atg cca tca gac agc     240
Gln Tyr Asn Cys Pro Gly Gln Tyr Thr Phe Ser Met Pro Ser Asp Ser
65                  70                  75                  80 cat gtt tct tca tgc tct gag gac tgg gtt ggc tac cag agg aaa tgc     288
His Val Ser Ser Cys Ser Glu Asp Trp Val Gly Tyr Gln Arg Lys Cys
                85                  90                  95 tac ttt att tct act gtg aag agg agc tgg act tca gcc caa aat gct     336
Tyr Phe Ile Ser Thr Val Lys Arg Ser Trp Thr Ser Ala Gln Asn Ala
            100                 105                 110 tgt tct gaa cat ggt gct act ctt gct gtc att gat tct gaa aag gac     384
Cys Ser Glu His Gly Ala Thr Leu Ala Val Ile Asp Ser Glu Lys Asp
        115                 120                 125 atg aac ttt cta aaa cga tac gca ggt aga gag gaa cac tgg gtt gga     432
Met Asn Phe Leu Lys Arg Tyr Ala Gly Arg Glu Glu His Trp Val Gly
    130                 135                 140 ctg aaa aag gaa cct ggt cac cca tgg aag tgg tca aat ggc aaa gaa     480
Leu Lys Lys Glu Pro Gly His Pro Trp Lys Trp Ser Asn Gly Lys Glu
145                 150                 155                 160 ttt aac aac tgg ttc aac gtt aca ggg tct gac aag tgt gtt ttt ctg     528
Phe Asn Asn Trp Phe Asn Val Thr Gly Ser Asp Lys Cys Val Phe Leu
                165                 170                 175 aaa aac aca gag gtc agc agc atg gaa tgt gag aag aat tta tac tgg     576
Lys Asn Thr Glu Val Ser Ser Met Glu Cys Glu Lys Asn Leu Tyr Trp
            180                 185                 190 ata tgt aac aaa cct tac aaa taa                                     600
Ile Cys Asn Lys Pro Tyr Lys
        195
```

<210> SEQ ID NO 20
<211> LENGTH: 199
<212> TYPE: PRT
<213> ORGANISM: homo sapiens

<400> SEQUENCE: 20

```
Met Ser Ser Glu Asn Cys Phe Val Ala Glu Asn Ser Ser Leu His Pro
1               5                   10                  15

Glu Ser Gly Gln Glu Asn Asp Ala Thr Ser Pro His Phe Ser Thr Arg
            20                  25                  30

His Glu Gly Ser Phe Gln Val Pro Val Leu Cys Ala Val Met Asn Val
        35                  40                  45

Val Phe Ile Thr Ile Leu Ile Ile Ala Leu Ile Ala Leu Ser Val Gly
    50                  55                  60

Gln Tyr Asn Cys Pro Gly Gln Tyr Thr Phe Ser Met Pro Ser Asp Ser
65                  70                  75                  80

His Val Ser Ser Cys Ser Glu Asp Trp Val Gly Tyr Gln Arg Lys Cys
                85                  90                  95

Tyr Phe Ile Ser Thr Val Lys Arg Ser Trp Thr Ser Ala Gln Asn Ala
            100                 105                 110
```

```
Cys Ser Glu His Gly Ala Thr Leu Ala Val Ile Asp Ser Glu Lys Asp
            115                 120                 125

Met Asn Phe Leu Lys Arg Tyr Ala Gly Arg Glu Glu His Trp Val Gly
        130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
        195

<210> SEQ ID NO 21
<211> LENGTH: 8
<212> TYPE: PRT
<213> ORGANISM: artificial
<220> FEATURE:
<223> OTHER INFORMATION: tag peptide

<400> SEQUENCE: 21

Asp Tyr Lys Asp Asp Asp Asp Lys
1               5

<210> SEQ ID NO 22
<211> LENGTH: 20
<212> TYPE: DNA
<213> ORGANISM: artificial
<220> FEATURE:
<223> OTHER INFORMATION: Designed oligonucleotide for use as a primer

<400> SEQUENCE: 22
ctaaggccaa ccgtgaaaag                                               20

<210> SEQ ID NO 23
<211> LENGTH: 20
<212> TYPE: DNA
<213> ORGANISM: artificial
<220> FEATURE:
<223> OTHER INFORMATION: Designed oligonucleotide for use as a primer

<400> SEQUENCE: 23
accagaggca tacagggaca                                               20

<210> SEQ ID NO 24
<211> LENGTH: 27
<212> TYPE: PRT
<213> ORGANISM: Artificial
<220> FEATURE:
<223> OTHER INFORMATION: an amino acid sequence highly homologous to a
      N-terminal partial amino acid sequence of Myl9, Myl12a, and Myl12
      b

<400> SEQUENCE: 24

Met Ser Ser Lys Arg Ala Lys Ala Lys Thr Thr Lys Lys Arg Pro Gln
1               5                   10                  15

Arg Ala Thr Ser Asn Val Phe Ala Met Phe Asp
            20                  25
```